United States Patent [19]

Schmidt et al.

[11] Patent Number: 4,697,018

[45] Date of Patent: Sep. 29, 1987

[54] 9-JULOLIDINYL DERIVATIVES AND PROCESS OF PREPARING THEM

[75] Inventors: Paul J. Schmidt, Sharonville; William M. Hung, Cincinnati, both of Ohio

[73] Assignee: The Hilton-Davis Chemical Co., Cincinnati, Ohio

[21] Appl. No.: 781,589

[22] Filed: Sep. 30, 1985

Related U.S. Application Data

[62] Division of Ser. No. 290,657, Aug. 6, 1981, Pat. No. 4,403,791.

[51] Int. Cl.$^4$ .................. C07D 455/02; C07D 209/02
[52] U.S. Cl. ....................................... 546/94; 548/455; 548/468; 548/511; 427/151
[58] Field of Search .................. 546/94; 548/455, 468, 548/511

[56] References Cited

U.S. PATENT DOCUMENTS 3,637,748  1/1972  Psaar et al. ...................... 260/326.15
3,642,823  2/1972  Raue et al. ...................... 260/326.15
3,995,088 11/1976  Garner et al. ...................... 428/323

OTHER PUBLICATIONS

Whitehead and Whitesilt, Journal of Medicinal Chemistry, 1974, vol. 17, No. 12, 1298–1304.
Morrison and Boyd, Org. Chem. 3rd Ed., p. 458.
Streitwieser et al, Intro. to Org. Chem. 2nd Ed., pp. 511–512.

Primary Examiner—Henry R. Jiles
Assistant Examiner—J. Richter
Attorney, Agent, or Firm—Terrence E. Miesle; Thomas L. Johnson; Paul E. Dupont

[57] ABSTRACT

The invention provides processes for the preparation of both known and novel [bis(substituted-aryl) (indolyl)]methanes and [(substituted-aryl) (heteryl) (indolyl)]methanes, useful as color formers, particularly in carbonless duplicating and thermal marking systems, which comprises the interaction of [bis(substituted-aryl) (phenylsulfonyl)]methanes and [(substituted-aryl) (heteryl) (phenylsulfonyl)]methanes with indoles in the presence of either an alkaline or an acidic catalyst.

7 Claims, No Drawings

9-JULOLIDINYL DERIVATIVES AND PROCESS OF PREPARING THEM

CROSS REFERENCE TO RELATED APPLICATIONS

This application is a division of our prior copending application Ser. No. 290,657, filed Aug. 6, 1981, and now U.S. Pat. No. 4,403,791 and is related to our prior copending application Ser. No. 501,309, filed Jun. 6, 1983, and now U.S. Pat. No. 4,558,137 which in turn is a division of our copending application Ser. No. 290,657, filed Aug. 6, 1981, and now U.S. Pat. No. 4,403,791.

BACKGROUND OF THE INVENTION (a) Field of the Invention

This invention relates to a novel process for the preparation of [bis(substituted aryl)(indolyl)]methanes and [(substituted aryl)(heteryl)(indolyl)]methanes useful in the art of carbonless duplicating as, for example, in pressure-sensitive systems and in thermal marking systems; and to novel [(aryl)(disubstituted aminoaryl)(indolyl)]methanes, [(aryl)(disubstituted aminoaryl)(indolyl carboxylic acid)]methanes and [(aryl)(julolidino)(indolyl)]methanes produced by said process.

(b) Description of the Prior Art

Several classes of organic compounds of widely diverse structural types are known to be useful as colorless precursors for carbonless duplicating systems. Among the more important classes, there may be named phenothiazines, for example, benzoyl leuco methylene blue; phthalides, for example, crystal violet lactone; fluorans, for example, 2'-anilino-6'-diethylaminofluoran and 2'-dibenzylamino-6'-diethylaminofluoran; arylsulfinate salts of Michler's Hydrol; and various other types of colorless precursors currently employed in commercially-accepted carbonless copy systems. Typical of the many such systems taught in the prior art are those described in U.S. Pat. Nos. 2,712,507, 2,800,457, 3,041,289 and 4,000,087, which issued July 5, 1955, July 23, 1957, June 26, 1962 and Dec. 28, 1976, respectively. Many of the color formers in the prior art suffer one or more disadvantages such as low tinctorial strength, poor light stability, low resistance to sublimation, low susceptibility to copiability of the color-developed form in standard office copying machines, for example, a xerographic type of copier, and low solubility in common organic solvents, the latter disadvantage thus requiring the use of specialized and expensive solvents in order to obtain microencapsulated solutions of sufficient concentration for use in pressure-sensitive copying systems.

In the prior art, benzoyl leuco methylene blue, related derivatives of phenothiazines, and analogous compounds derived from phenothiazines have been used as slow developing color formers for use in carbonless duplicating systems in combination with additional art recognized instant color-forming compounds.

One of the oldest combinations of color-forming compounds used in pressure-sensitive systems is a mixture of crystal violet lactone and benzoyl leuco methylene blue. The crystal violet lactone is responsible for providing the initial image which is, however, very unstable to light and moisture. These deficiencies are overcome by the use of benzoyl leuco methylene blue which develops slowly upon exposure to air, providing a green-blue image to augment or replace that of the fading crystal violet lactone. The developed image of the benzoyl leuco methylene blue is extremely light stable, but is rather green in shade, is lacking in contrast quality, and therefore is unsatisfactory when multiple copies are required. Further, it does not possess adequate xerographic copiability on the commercially-available reproduction machines.

The following items to date appear to constitute the most relevant prior art with regard to the instant invention.

U.S. Pat. No. 3,637,748, issued Jan. 25, 1972, discloses and claims a heteryl methane compound with is free of sulphonic acid groups and has the formula

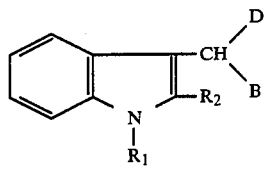

wherein $R_1$ is hydrogen or methyl; $R_2$ is methyl or phenyl; B stands for a member selected from the group consisting of phenyl, nitrophenyl, chlorophenyl, dichlorophenyl, methoxyphenyl, methylphenyl, hydroxyphenyl, thienyl-2, and furyl-2; D stands for a member selected from the group consisting of 4-methylquinolinyl-methosulphate, 1,2,3,3-tetramethyldihydroindolyl, 1-phenyl-3-methylpyrazolone-(5)-yl, 1-phenyl-2,3-dimethyl-pyrazolone-(5)-yl, substituted naphthyl, substituted phenyl, substituted chlorophenyl, substituted methylphenyl, substituted hydroxyphenyl and substituted ethoxyphenyl, wherein the substituent is located in the 4-position relative to the position at which the CH-group is bound and is a member selected from the group consisting of phenylamino, ethoxyphenyl, amino, methylphenylamino, methylethoxyphenylamino, piperidino, morpholino, mono-alkylamino wherein the alkyl portion contains 1–4 carbon atoms, di-lower alkylamino wherein the lower alkyl portion contains 1–2 carbon atoms, and said mono-alkylamino and said di-lower alkylamino substituted by a member of the group consisting of hydroxy, chloro, cyano and dimethylamino. The heteryl methane compounds are disclosed as being valuable dyestuff intermediates.

U.S. Pat. No. 3,642,823, issued Feb. 15, 1972, discloses and claims an aminodiphenyl-indolyl-methane dyestuff free of sulfonic acid and carboxylic acid groups having the formula

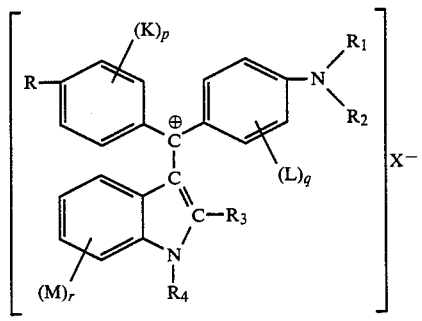

wherein R is hydrogen, lower alkyl containing 1–5 carbon atoms, nitro, cyano, benzyl, phenyl, carboxylic acid methyl ester, carboxylic acid ethyl ester, unsubstituted carbonamido, substituted carbonamido containing N-substituents selected from the group consisting of lower alkyl, and lower alkyl substituted with Cl, Br, or OH, methylsulfonyl, ethylsulfonyl, phenylsulfonyl, p-toluene sulfonyl, benzoyl, or acetyl; $R_1$ and $R_2$ are both hydrogen; or $R_1$ is unsubstituted lower alkyl containing 1-5 carbon atoms, substituted lower alkyl containing 1-5 carbon atoms and substituted with Cl, Br or OH, benzyl, naphthyl, phenyl or phenyl substituted with Cl, Br, lower alkyl or lower alkoxy and $R_2$ is unsubstituted lower alkyl containing 1-5 carbon atoms, substituted lower alkyl containing 1-5 carbon atoms and substituted with Cl, Br, OH, or CN or benzyl; $R_3$ is hydrogen, lower alkyl containing 1-5 carbon atoms, lower alkoxy, phenyl, phenyl substituted with chlorine, bromine, lower alkyl or lower alkoxy or carboxylic acid methyl or ethyl ester; $R_4$ is hydrogen, lower alkyl containing 1-5 carbon atoms, lower alkyl containing 1-5 carbon atoms substituted with CN, or benzyl; K, L and M are independently selected from the group consisting of hydrogen, lower alkyl, lower alkoxy, nitro, Cl, and Br, or two of the substituents M are fused to form a naphthalene nucleus; p, q and r are 1 or 2; and X is a substantially colorless anion which does not impair the solubility of the dyestuff in an undesirable manner. The aminodiphenyl-indolyl-methane dyestuffs are described as being useful in the dyeing and printing of materials of leather, tannin-treated cotton, cellulose acetate, synthetic superpolyamides and superurethanes as well as for the dyeing of lignin-containing fibres, such as coconut fibres, jute and sisal. They are also suitable for the production of liquid writing inks, stamping inks, ball point pen pastes and they may also be used in offset printing. Above all they are eminently suitable for the dyeing and printing of materials which are composed partially or completely of polymerized acrylonitrile and/or vinylidene cyanide or which are composed partially or completely of acid-modified aromatic polyesters, such as sulphonic acid group-containing polyethylene terephthalate.

U.S. Pat. No. 3,995,088, issued Nov. 30, 1976, discloses and claims a pressure-sensitive recording material comprising at least one pair of paper sheets containing at least two color formers, dissolved in an organic solvent, and an electron-accepting substance wherein at least one color former is a leuco methylene dyestuff of the formula $$Y-\underset{Z}{CH}-Y$$

wherein Y represents an amino-substituted phenyl residue of the formula

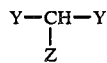

or an indolyl residue of the formula

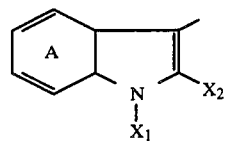

wherein $R_1$ and $R_2$, independently of the other represent hydrogen, alkyl with 1-12 carbon atoms, alkoxyalkyl with 2-8 carbon atoms, benzyl or phenyl; $R_3$ is hydrogen, halogen, nitro, alkyl having 1-4 carbon atoms or alkoxy having 1-4 carbon atoms; $X_1$ represents hydrogen, alkyl with 1-12 carbon atoms, alkenyl with at most 12 carbon atoms or benzyl; $X_2$ represents hydrogen, alkyl with 1-12 carbon atoms or phenyl; the ring A is unsubstituted or substituted by cyano, nitro, halogen, alkyl having 1-4 carbon atoms, alkoxy having 1-4 carbon atoms or acyl with 1-8 carbon atoms; and Z represents alkyl with 1-12 carbon atoms, alkenyl with at most 12 carbon atoms, aryl, aralkyl, a heterocyclic radical or the residue of an organic, particularly aliphatic or cycloaliphatic, compound having a ketomethylene group. The other color former is selected from the group consisting of crystal violet lactone, benzoyl leuco methylene blue, diamino substituted fluoran compounds, 3-phenyl-3-indolylphthalides or 3,3-bis-indolylphthalides or their mixtures thereof.

Whitehead and Whitesilt in the Journal of Medicinal Chemistry 1974 Vol. 17, No. 12, 1298-1304 (1974) describe the preparation and physical characteristics of [bis(phenyl)(2-carboxyindol-3-yl)]methane from the interaction of 2-carboxyindole and benzhydrol in glacial acetic acid. The compound and similar compounds were screened for antimicrobial activity. Toxicity, behavioral effects, antiviral activity, antiinflammatory properties, antispasmatic activity and general endocrine properties of the (diarylmethyl)indoles are described.

(c) Prior Publication

West German Offenlegungsschrift 2,917,271, which was published on Nov. 6, 1980, describes pressure- and heat-sensitive copy material, characterized by the fact that it contains a color component of the formula

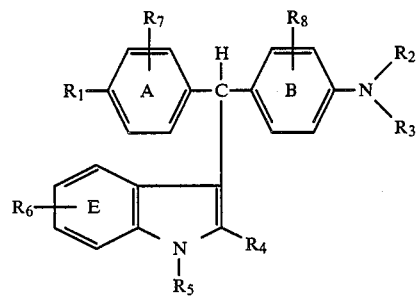

in which $R^1$ designates hydrogen, hydroxy, $C_1$ to $C_6$ alkoxy, $C_2$ to $C_6$ alkenyloxy, cycloheyloxy, cyclopentyloxy, possibly benzyloxy, phenylethyloxy, phenyloxy, naphthyloxy, phenylthio or naphthylthio, $C_1$ to $C_6$ alkylthio substituted by $C_1$ to $C_4$ alkyl, $C_1$ to $C_4$ alkoxy or halogen; $R^2$ and $R^3$ independently of one another designate hydrogen, or $C_1$ to $C_6$ alkyl possibly substituted by $C_1$ to $C_4$ alkoxy, $C_1$ to $C_4$ alkyl, carbonyloxy, hydroxy, halo or cyano, or benzyl, phenylethyl, phenyl or naphthyl, cyclopentyl or cyclohexyl, substituted by $C_1$ to $C_4$ alkyl, $C_1$ to $C_4$ alkoxy or halogen, or $R^2$ and $R^3$ along with the nitrogen atom designate as pyrrolidine, pyrazoline, piperidine or morpholine ring, or $R^2$ along with the nitrogen atom and the ring B designate an indoline or tetrahydroquinoline ring, wherein the rings mentioned can be substituted by methyl or phenyl; $R^4$ designates $C_1$ to $C_4$ alkyl or phenyl; $R^5$ designates hydrogen, possibly $C_1$ to $C_{22}$ alkyl, $C_2$ to $C_4$ alkenyl, cyclohexyl substituted by cyano, chloro or hydroxy, phenyl or benzyl substituted by methyl, ethyl, methoxy, ethoxy or chlorine; $R^6$, $R^7$ and $R^8$ independently of one another designate hydrogen, methyl, ethyl, methoxy, ethoxy or chlorine. This reference appeared subsequent to applicants' invention described herein and less than one year prior to the filing date of this application.

SUMMARY OF THE INVENTION

In its process aspect, the invention relates to the process for producing a [(X)(Y)(indolyl)]methane which comprises interacting a [(X)(Y)(R-phenylsulfonyl)]methane with an indole.

In one of its composition of matter aspects, the invention relates to certain [(2-$R^1$-3-$R^2$-4-$R^{3'}$-phenyl)(2-$R^4$-4-$R^5$-phenyl)(1-$R^{9'}$-2-$R^{10}$-5/6-$R^{11}$-indol-3-yl)]methanes useful as colorless precursors in carbonless duplicating systems.

In a second composition of matter aspect, the invention relates to certain [(2-$R^1$-3-$R^2$-4-$R^3$-phenyl)(2-$R^4$-4-$R^5$-phenyl)(1-$R^9$-2-B"O-carbonyl-5/6-$R^{11}$-indol-3-yl)]methanes useful as colorless precursors in carbonless duplicating systems.

In a third composition of matter aspect, the invention relates to certain [(2-$R^1$-3-$R^2$-4-$R^3$-phenyl)(9-julolidinyl)(1-$R^9$-2-$R^{10}$-5/6-$R^{11}$-indol-3-yl)]methanes useful as colorless precursors in carbonless duplicating systems.

DETAILED DESCRIPTION INCLUSIVE OF THE PREFERRED EMBODIMENTS

More specifically, this invention in one of its process aspects resides in the novel process for the preparation of methanes, which are particularly useful as colorless precursors in the art of carbonless duplicating and thermal marking, and provides for the preparation of [(X)(Y)(1-$R^9$-2-$R^{10}$-5/6-$R^{11}$-indol-3-yl)]methanes having the formula

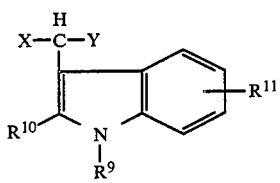

Formula I which comprises interacting a [(X)(Y)(R-phenylsulfonyl)]methane having the formula

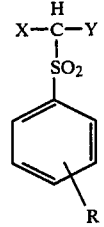

Formula II with an indole of the formula

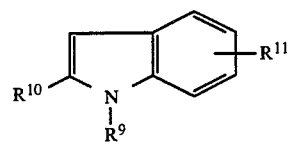

Formula III in the presence of an alkaline or an acid catalyst wherein: x represents a moiety selected from the class having the formulas

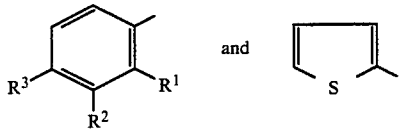

in which $R^1$ represents hydrogen, $C_1$ to $C_3$ alkyl, non-tertiary $C_1$ to $C_4$ alkoxy, halo or dialkylamino in which alkyl is non-tertiary $C_1$ to $C_4$ alkyl, $R^2$ represents hydrogen or nitro, and $R^3$ represents hydrogen, $C_1$ to $C_3$ alkyl, non-tertiary $C_1$ to $C_4$ alkoxy, halo, nitro, dialkylamino or N-alkylbenzylamino in which alkyl is non-tertiary $C_1$ to $C_4$ alkyl and benzyl may be substituted in the benzene ring by one or two of halo or $C_1$ to $C_3$ alkyl; Y represents a moiety selected from the group having the formulas

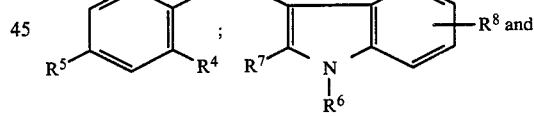

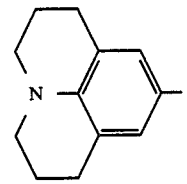

in which: $R^4$ represents hydrogen, $C_1$ to $C_3$ alkyl, non-tertiary $C_1$ to $C_4$ alkoxy, halo or dialkylamino in which alkyl is non-tertiary $C_1$ to $C_4$ alkyl; $R^5$ represents hydrogen, $C_1$ to $C_3$ alkyl, non-tertiary $C_1$ to $C_4$ alkoxy, halo, dialkylamino or N-alkylbenzylamino in which alkyl is non-tertiary $C_1$ to $C_4$ alkyl and benzyl may be substituted in the benzene ring by one or two of $C_1$ to $C_3$ alkyl; $R^6$ represents hydrogen, non-tertiary $C_1$ to $C_{18}$ alkyl, $C_2$ to $C_4$ alkenyl, benzyl or benzyl substituted in the benzene ring by one or two of $C_1$ to $C_3$ alkyl or halo; $R^7$ represents hydrogen, $C_1$ to $C_3$ alkyl or phenyl; and $R^8$ represents one or two of hydrogen, $C_1$ to $C_3$ alkyl, $C_1$ to $C_3$ alkoxy, halo or nitro; $R^9$ represents hydrogen, non-tertiary $C_1$ to $C_{18}$ alkyl, $C_2$ to $C_4$ alkenyl, benzyl or benzyl substituted in the benzene ring by one or two of halo or $C_1$ to $C_3$ alkyl; $R^{10}$ represents hydrogen, $C_1$ to $C_3$ alkyl, phenyl or carboxy; R represents one or two of hydrogen, non-tertiary $C_1$ to $C_{12}$ alkyl, $C_1$ to $C_3$ alkoxy, halo, nitro or acetamido.

In a first particular embodiment in accordance with its first process aspect, the invention sought to be patented resides in the novel process for preparing a [(2-$R^1$-3-$R^2$-4-$R^3$-phenyl)(2-$R^4$-4-$R^5$-phenyl)(1-$R^9$-2-$R^{10}$-5/6-$R^{11}$-indol-3-yl)]methane having the formula

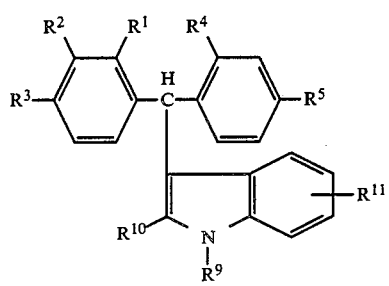

Formula IV wherein $R^1$, $R^2$, $R^3$, $R^4$, $R^5$, $R^9$, $R^{10}$ and $R^{11}$ each have the same respective meanings given in Formula I.

In a second particular embodiment in accordance with its first process aspect, the invention sought to be patented resides in the novel process for preparing a [(2-$R^1$-3-$R^2$-4-$R^3$-phenyl)(1-$R^6$-2-$R^7$-5/6-$R^8$-indol-3-yl)(1-$R^9$-2-$R^{10}$-5/6-$R^{11}$-indol-3-yl)]methane having the formula

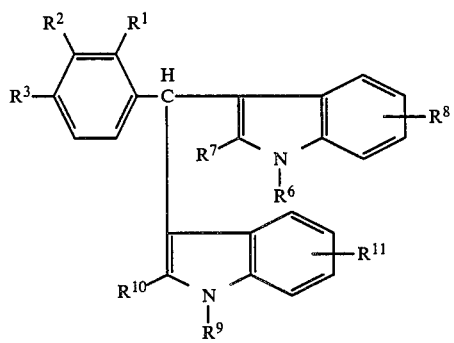

Formula V wherein $R^1$, $R^2$, $R^3$, $R^6$, $R^7$, $R^8$, $R^9$, $R^{10}$ and $R^{11}$ each have the same respective meanings given in Formula I.

In a third particular embodiment in accordance with its first process aspect, the invention sought to be patented resides in the novel process for preparing a [(2-$R^1$-3-$R^2$-4-$R^3$-phenyl)(9-julolidinyl)(1-$R^9$-2-$R^{10}$-5/6-$R^{11}$-indol-3-yl)]methane having the formula

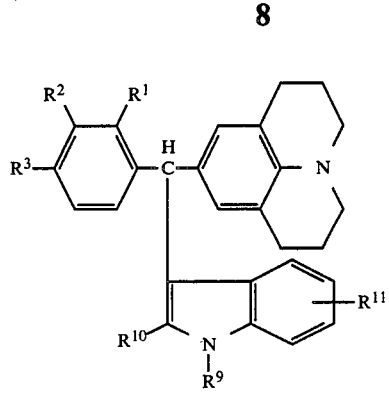

Formula VI wherein $R^1$, $R^2$, $R^3$, $R^9$, $R^{10}$ and $R^{11}$ each have the same respective meanings given in Formula I.

In a fourth particular embodiment in accordance with its first process aspect, the invention sought to be patented resides in the novel process for preparing a [(2-thienyl) (1-$R^6$-2-$R^7$-5/6-$R^8$-indol-3-yl)(1-$R^9$-2-$R^{10}$-5/6-$R^{11}$-indol-3-yl)]methane having the formula

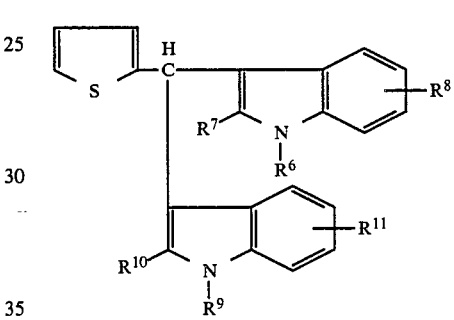

Formula VII wherein $R^6$, $R^7$, $R^8$, $R^9$, $R^{10}$ and $R^{11}$ each have the same respective meanings given in Formula I.

This invention, in its second process aspect, resides in the process for preparing a [(X)(Y)(1-$R^9$-2-B'O-carbonyl-5/6-$R^{11}$-indol-3-yl)]methane having the formula

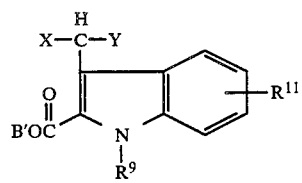

Formula VIII which comprises esterifying the corresponding [(X) (Y) (1-$R^9$-2-carboxy-5/6-$R^{11}$-indol-3-)]methane with an appropriate compound selected from the group consisting of dimethylsulfate, diethylsulfate or B'-halogen in the presence of an alkali metal hydroxide or carbonate wherein: X represents a moiety selected from the group having the formulas

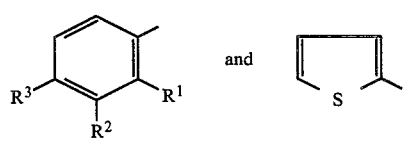

in which $R^1$ represents hydrogen, $C_1$ to $C_3$ alkyl, non-tertiary $C_1$ to $C_4$ alkoxy, halo or dialkylamino in which alkyl is non-tertiary $C_1$ to $C_4$ alkyl; $R^2$ represents hydrogen or nitro; and $R^3$ represents hydrogen, $C_1$ to $C_3$ alkyl, non-tertiary $C_1$ to $C_4$ alkoxy, halo, nitro, dialkylamino or N-alkylbenzylamino in which alkyl is non-tertiary $C_1$ to $C_4$ alkyl and benzyl is substituted in the benzene ring by one or two of halo or $C_1$ to $C_3$ alkyl; Y represents a moiety selected from the group having the formulas

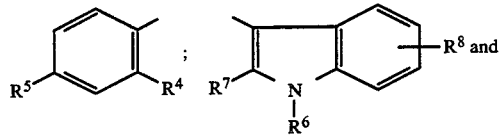

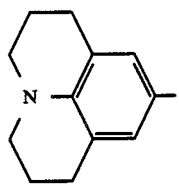

in which $R^4$ represents hydrogen, $C_1$ to $C_3$ alkyl, non-tertiary $C_1$ to $C_4$ alkoxy, halo or dialkylamino in which alkyl is non-tertiary $C_1$ to $C_4$ alkyl; $R^5$ represents hydrogen, $C_1$ to $C_3$ alkyl, non-tertiary $C_1$ to $C_4$ alkoxy, halo, dialkylamino or N-alkylbenzylamino in which alkyl is non-tertiary $C_1$ to $C_4$ alkyl and benzyl may be substituted in the benzene ring by one or two of halo or $C_1$ to $C_3$ alkyl; $R^6$ represents hydrogen, non-tertiary $C_1$ to $C_{18}$ alkyl, $C_2$ to $C_4$ alkenyl, benzyl or benzyl substituted in the benzene ring by one or two of $C_1$ to $C_3$ alkyl or halo; $R^7$ represents hydrogen, $C_1$ to $C_3$ alkyl or phenyl; $R^8$ represents one or two of hydrogen, $C_1$ to $C_3$ alkyl, $C_1$ to $C_3$ alkoxy, halo or nitro; $R^9$ represents hydrogen, non-tertiary $C_1$ to $C_{18}$ alkyl, $C_2$ to $C_4$ alkenyl, benzyl or benzyl substituted in the benzene ring by one or two of halo or $C_1$ to $C_3$ alkyl; $R^{11}$ represents one or two of hydrogen, $C_1$ to $C_3$ alkyl, $C_1$ to $C_3$ alkoxy, halo or nitro; and B′ represents non-tertiary $C_1$ to $C_{18}$ alkyl, $C_2$ to $C_8$ alkenyl, benzyl or benzyl substituted in the benzene ring by one or two of halo or $C_1$ to $C_3$ alkyl.

In a particular embodiment in accordance with its second process aspect, the invention sought to be patented resides in the novel process for preparing a [(2-$R^1$-3-$R^2$-4-$R^3$-phenyl)(2-$R^4$-4-$R^5$-phenyl)(1-$R^9$-2-B′O-carbonyl-5/6-$R^{11}$-indol-3-yl)]methane having the formula

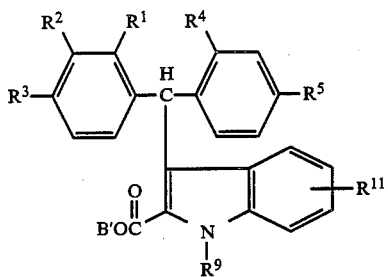

Formula IX wherein $R^1$, $R^2$, $R^3$, $R^4$, $R^5$, $R^9$, $R^{11}$ and B′ each have the same respective meanings given in Formula VIII.

This invention, in the first of its composition of matter aspects, resides in the novel methanes, which are particularly useful as colorless precursors in the art of carbonless duplicating and thermal marking, and which are [(2-$R^1$-3-$R^2$-4-$R^{3'}$-phenyl)(2-$R^4$-4-$R^5$-phenyl)(1-$R^{9'}$-2-$R^{10}$-5/6-$R^{11}$-indol-3-yl)]methanes having the formula

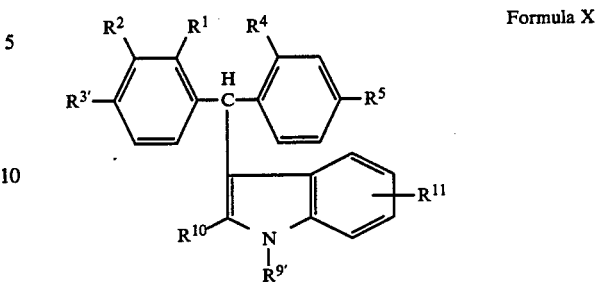

Formula X wherein $R^1$ represents hydrogen, $C_1$ to $C_3$ alkyl, non-tertiary $C_1$ to $C_4$ alkoxy, halo or dialkylamino in which alkyl is non-tertiary $C_1$ to $C_4$ alkyl; $R^2$ represents hydrogen or nitro; $R^{3'}$ represents hydrogen, $C_1$ to $C_3$ alkyl, non-tertiary $C_1$ to $C_4$ alkoxy, halo, nitro or when $R^5$ is N-alkylbenzylamino, $R^{3'}$ further represents dialkylamino or N-alkylbenzylamino in which alkyl is non-tertiary $C_1$ to $C_4$ alkyl and benzyl may be substituted in the benzene ring by one or two of halo or $C_1$ to $C_3$ alkyl; $R^4$ represents hydrogen, $C_1$ to $C_3$ alkyl, non-tertiary $C_1$ to $C_4$ alkoxy, halo or dialkylamino in which alkyl is non-tertiary $C_1$ to $C_4$ alkyl; $R^5$ represents dialkylamino or N-alkylbenzylamino in which alkyl is non-tertiary $C_1$ to $C_4$ alkyl and benzyl may be substituted in the benzene ring by one or two of halo or $C_1$ to $C_3$ alkyl; $R^{9'}$ represents $C_2$ to $C_{18}$ alkyl, $C_2$ to $C_4$ alkenyl, benzyl or benzyl substituted in the benzene ring by one or two of halo or $C_1$ to $C_3$; $R^{10}$ represents hydrogen, $C_1$ to $C_3$ alkyl or phenyl; and $R^{11}$ represents one or two of hydrogen, $C_1$ to $C_3$ alkyl, $C_1$ to $C_3$ alkoxy, halo or nitro.

This invention, in its second composition of matter aspect, resides in the novel methanes, which are particularly useful as colorless precursors in the art of carbonless duplicating and thermal marking, and which are [(2-$R^1$-3-$R^2$-4-$R^3$-phenyl)(2-$R^4$-4-$R^5$-phenyl)(1-$R^9$-2-B″O-carbonyl-5/6-$R^{11}$-indol-3-yl)]methanes having the formula

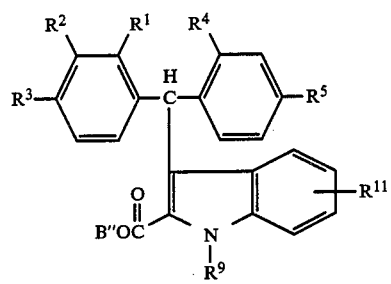

Formula XI wherein $R^1$ represents hydrogen, $C_1$ to $C_3$ alkyl, non-tertiary $C_1$ to $C_4$ alkoxy, halo or dialkylamino in which alkyl is non-tertiary $C_1$ to $C_4$ alkyl; $R^2$ represents hydrogen or nitro; $R^3$ represents hydrogen, $C_1$ to $C_3$ alkyl, non-tertiary $C_1$ to $C_4$ alkoxy, halo, dialkylamino or N-alkylbenzylamino in which alkyl is non-tertiary $C_1$ to $C_4$ alkyl and benzyl may be substituted in the benzene ring by one or two of halo or $C_1$ to $C_3$ alkyl; $R^4$ represents hydrogen, non-tertiary $C_1$ to $C_4$ alkyl, non-tertiary $C_1$ to $C_4$ alkoxy, halo or dialkylamino in which alkyl is non-tertiary $C_1$ to $C_4$ alkyl; $R^5$ represents dialkylamino or N-alkylbenzylamino in which alkyl is non-tertiary $C_1$ to $C_4$ alkyl and benzyl may be substituted in the benzene ring by one or two of halo or $C_1$ to $C_3$ alkyl; $R^9$ represents hydrogen, $C_1$ to $C_{18}$ alkyl, $C_2$ to $C_4$ alkenyl, benzyl and benzyl substituted in the benzene ring by one or two of halo; $R^{11}$ represents one or two of hydrogen, $C_1$ to $C_3$ alkyl, $C_1$ to $C_3$ alkoxy, halo or nitro; and $B''$ represents hydrogen, $C_1$ to $C_{18}$ alkyl, $C_2$ to $C_8$ alkenyl, benzyl or benzyl substituted in the benzene ring by one or two of halo or $C_1$ to $C_3$ alkyl.

This invention, in its third composition of matter aspect, resides in the novel methanes, which are particularly useful as colorless precursors in the art of carbonless duplicating and thermal marking, and which are [(2-$R^1$-3-$R^2$-4-$R^3$-phenyl)(9-julolidinyl)(1-$R^9$-2-$R^{10}$-5/6-$R^{11}$-indol-3-yl)]methanes having the formula

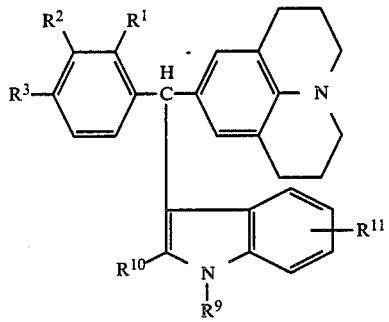

Formula XII wherein $R^1$ represents hydrogen, $C_1$ to $C_3$ alkyl, non-tertiary $C_1$ to $C_4$ alkoxy, halo or dialkylamino in which alkyl is non-tertiary $C_1$ to $C_4$ alkyl; $R^2$ represents hydrogen or nitro; $R^3$ represents hydrogen, $C_1$ to $C_3$ alkyl, non-tertiary $C_1$ to $C_4$ alkoxy, halo, nitro, dialkylamino or N-alkylbenzylamino in which alkyl is non-tertiary $C_1$ to $C_4$ alkyl and benzyl may be substituted in the benzene ring by one or two of halo or alkyl; $R^9$ represents hydrogen, $C_1$ to $C_{18}$ alkyl, $C_2$ to $C_4$ alkenyl, benzyl or benzyl substituted in the benzene ring by one or two of halo or $C_1$ to $C_3$ alkyl; $R^{10}$ represents hydrogen, $C_1$ to $C_3$ alkyl, phenyl or —$COB''$ in which $B''$ represents hydrogen, $C_1$ to $C_{18}$ alkyl, $C_2$ to $C_8$ alkenyl, benzyl or benzyl substituted in the benzene ring by $C_1$ to $C_{12}$ alkyl, halo or $C_1$ to $C_8$ alkoxy; and $R^{11}$ represents one or two of hydrogen, $C_1$ to $C_3$ alkyl, $C_1$ to $C_3$ alkoxy, halo or nitro.

In the first of its article of manufacture aspects, the invention sought to be patented resides in a pressure-sensitive carbonless duplicating system or a thermal marking system containing a support sheet coated with a layer containing a color-forming substance comprising a compound having the formula

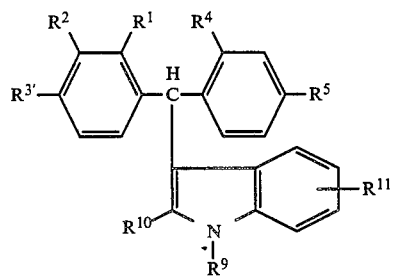

Formula XIII wherein $R^1$ represents hydrogen, $C_1$ to $C_3$ alkyl, non-tertiary $C_1$ to $C_4$ alkoxy, halo or dialkylamino in which alkyl is non-tertiary $C_1$ to $C_4$ alkyl; $R^2$ represents hydrogen or nitro; $R^{3'}$ represents hydrogen, $C_1$ to $C_3$ alkyl, non-tertiary $C_1$ to $C_4$ alkoxy, halo, nitro or when $R^5$ is N-alkylbenzylamino, $R^{3'}$ further represents dialkylamino or N-alkylbenzylamino in which alkyl is non-tertiary $C_1$ to $C_4$ alkyl and benzyl may be substituted in the benzene ring by one or two of halo or $C_1$ to $C_3$ alkyl; $R^4$ represents hydrogen, non-tertiary $C_1$ to $C_4$ alkyl, non-tertiary $C_1$ to $C_4$ alkoxy, halo or dialkylamino in which alkyl is non-tertiary $C_1$ to $C_4$ alkyl; $R^5$ represents dialkylamino or N-alkylbenzylamino in which alkyl is non-tertiary $C_1$ to $C_4$ alkyl and benzyl may be substituted in the benzene ring by one or two of halo or $C_1$ to $C_3$ alkyl; $R^9$ represents hydrogen, non-tertiary $C_1$ to $C_{18}$ alkyl, $C_2$ to $C_4$ alkenyl, benzyl or benzyl substituted in the benzene ring by one or two of halo or $C_1$ to $C_3$ alkyl; $R^{10}$ represents hydrogen, $C_1$ to $C_3$ alkyl or phenyl; and $R^{11}$ represents one or two of hydrogen, $C_1$ to $C_3$ alkyl, $C_1$ to $C_3$ alkoxy, halo or nitro.

In a second of its article of manufacture aspects, the invention sought to be patented resides in a pressure-sensitive carbonless duplicating system or a thermal marking system containing a support sheet coated with a layer containing as a color-forming substance a [(2-$R^1$-3-$R^2$-4-$R^3$-phenyl)(2-$R^4$-4-$R^5$-phenyl)(1-$R^9$-2-$B''$O-carbonyl-5/6-$R^{11}$-indol-3-yl)]methane according to Formula XI or a [(2-$R^1$-3-$R^2$-4-$R^3$-phenyl)(9-julolidinyl)(1-$R^9$-2-$R^{10}$-5/6-$R^{11}$-indol-3-yl)]methane according to Formula XII wherein $R^1$, $R^2$, $R^3$, $R^4$, $R^5$, $R^9$, $R^{10}$, $R^{11}$ and $B''$ each have the same respective meanings given in relation to Formula XI or Formula XII.

A particular embodiment sought to be patented in accordance with its article of manufacture aspects resides in a pressure-sensitive transfer sheet, adapted for use with a receiving sheet having an electron accepting layer, comprising a support sheet coated on one side with a layer of pressure-rupturable microcapsules containing a liquid solution of a color-forming substance comprising at least one compound depicted by Formula XI, by Formula XII or by Formula XIII.

Another particular embodiment sought to be patented in accordance with its article of manufacture aspects resides in a heat responsive record material comprising a support sheet coated on one side with a layer containing a mixture comprising at least one color-forming compound having Formula XI, Formula XII or Formula XIII and an acidic developer arranged such that application of heat will produce a mark-forming reaction between the color-forming compound and the acidic developer.

Still another particular embodiment sought to be patented in accordance with its article of manufacture aspects resides in a heat responsive record material comprising a support sheet coated on one side with a layer containing a mixture comprising at least one color-forming compound having Formula XI, Formula XII or Formula XIII and an oxidizing agent arranged such that application of heat will produce a mark-forming reaction between the color-forming compound and the oxidizing agent.

As used herein the term "halo" includes chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substituents are also satisfactory.

The term "dialkylamino in which alkyl is non-tertiary $C_1$ to $C_4$ alkyl" denotes saturated, acyclic groups which may be straight or branched as exemplified by dimethylamino, diethylamino, ethylmethylamino, dipropylamino, dibutylamino, isobutylmethylamino and the like.

The term "N-alkylbenzylamino in which alkyl is non-tertiary $C_1$ to $C_4$ alkyl and benzyl may be substituted in the benzene ring by one or two of halo or $C_1$ to $C_3$ alkyl" denotes an amino moiety which is substituted with acyclic group which may be straight or branched and one benzyl group as exemplified by N-methylbenzylamino, N-ethylbenzylamino, N-propylbenzylamino, N-butylbenzylamino, N-ethyl(2,5-dimethylbenzyl)amino, N-ethyl(4-chlorobenzyl)amino and the like.

As used herein the terms "$C_1$ to $C_3$ alkyl", "non-tertiary $C_1$ to $C_4$ alkyl", "non-tertiary $C_1$ to $C_{12}$ alkyl" and "non-tertiary $C_1$ to $C_{18}$ alkyl" denote saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, 2-ethylhexyl, nonyl, 3-ethylheptyl, n-decyl, n-undecyl, n-dodecyl, n-tridecyl, n-octodecyl, 1,3,5-trimethylhexyl, 1,5-dimethyl-4-ethylhexyl, 5-methyl-2-butyl-hexyl, 2-propylnonyl, 2-butyloctyl, 2-pentanonyl, 1,2-dimethylhexadecyl and the like.

The terms "$C_1$ to $C_3$ alkoxy" and "non-tertiary $C_1$ to $C_4$ alkoxy" include saturated acyclic, straight or branched-chained groups such as methoxy, ethoxy, propoxy, isopropoxy, butoxy, sec-butoxy, and isobutoxy.

As used herein, the terms "$C_2$ to $C_4$ alkenyl" and "$C_2$ to $C_8$ alkenyl" mean monovalent aliphatic radicals possessing a single double bond, for example, ethenyl (or vinyl), 2-propenyl (or allyl), 1-methylethenyl (or isopropenyl), 2-methyl-2-propenyl, 2-methyl-1-propenyl, 2-butenyl, 3-butenyl, 1-pentenyl, 2-pentenyl, 3-methyl-2-butenyl, 2-methyl-1-butenyl (isoamylenyl), 3-methyl-1-butenyl, 1-hexenyl, 2-hexenyl, 3-hexenyl, 2-heptenyl and 1-octenyl.

As used herein, the term "acid catalyst" denotes any material which is acidic in nature. Among these catalysts are acidic halide Lewis acid catalysts, Bronsted acid catalysts, acidic oxide catalysts, acidic cation exchange resin catalysts, and any organic or inorganic material which is capable of partial hydrolysis in the reaction medium to form acidic conditions. Examples of catalysts are hydrobromic acid, hydrochloric cid, hydriodic acid, sulfuric acid, phosphoric acid, nitric acid, fluoroboric acid, perchloric acid, arylsulfonic acids and alkylsulfonic acids, for example, p-toluenesulfonic acid, methanesulfonic acid, formic acid, acetic acid, glycolic acid, lactic acid, propionic acid, monochloroacetic acid, dichloroacetic acid, trichloroacetic acid, trifluoroacetic acid, malonic acid, citric acid, fumaric acid, benzoic acid, salicylic acid, picric acid, trimellitic acid, aluminum chloride, ferric chloride, zinc chloride, stannic chloride, phosphorus trichloride, phosphorus pentachloride, boron trifluoride etherate, phosphorous oxychloride, thionyl chloride, ferric oxide, aluminum oxide, phosphorus pentaoxide, benzoyl chloride, benzoyl peroxide, potassium fluoride, sulfonated coals, sulfonated phenol-formaldehyde resins, sulfonated divinylbenzene cross linked polymers and exchangers with carboxyl group, phenol group or alumina-silicate skeleton.

As used herein the term "alkaline catalyst" is intended to be inclusive of both inorganic and organic basic compounds. Among these catalysts are sodium hydroxide, potassium hydroxide, lithium hydroxide, sodium carbonate, potassium carbonate, lithium carbonate, ammonium hydroxide, tetramethylammonium hydroxide, tetraethylammonium hydroxide, tetrabutylammonium hydroxide, quinuclidine, 1,4-diazobicyclo[2,2,2]-octane, triethanolamine, triethylamine and urea.

As used herein the term "reaction medium" denotes any non-solvent or solvent capable of dispersing, partially dissolving or completely dissolving the reactants thus providing a fluid medium for these reactants to interact forming the desired methanes. Examples of chemical compounds which may be utilized singly or in a combination as a "reaction medium" are methyl alcohol, ethyl alcohol, isopropyl alcohol, ethylene glycol, ethylene glycol monoethyl ether, propylene glycol, diethylene glycol, diethylene glycol dimethyl ether, acetonitrile, ethylene dichloride N,N-dimethylformamide, N,N-dimethylaniline, isopropyl crown ether, acetone, ethylmethylketone, propylmethylketone, butylmethylketone and water.

The compounds of Formula I, (which of course encompass the novel compounds of Formula X, Formula XI and Formula XII) and those of Formula XIII, hereinabove are essentially colorless in the depicted form. When contacted with an acidic medium, for example, silica gel or one of the types ordinarily employed in pressure-sensitive carbonless duplicating systems such as silton clay or phenolic resins, the compounds of Formula I develop green-gray, brown, purple, violet, blue-red, red, and gray to black-colored images in the air or in the presence of an oxidizing agent. These developed images are very insensitive to light, are of good to excellent tinctorial strength, possess excellent xerographic copiability and enhanced solubility in common organic solvents. The compounds are thus highly suitable for use as colorless precursors, that is, color-forming substances in pressure-sensitive carbonless duplicating systems. The darker violet colors can be used alone as color formers to produce images which are readily copiable, whereas the brown, red and blue colors can be used as toners in admixture with other color formers to produce images of a neutral shade which desirably are readily copiable by xerographic means.

The methane compounds of Formulas I, X, XI, XII and XIII are generally used in admixture with one or more other color formers selected from the classes consisting of phthalides, for example, crystal violet lactone; fluorans, for example, 2'-anilino-6'-diethylaminofluoran and 2'-dibenzylamino-6'-diethylaminofluoran; phenothiazines, for example, benzoyl leuco methylene blue; arylsulfinate salts of Michler's Hydrol; and various other types of colorless precursors currently employed in commercially-accepted carbonless copy systems.

The compounds of this invention may be incorporated in any of the commercially-accepted systems known in the carbonless duplicating art. A typical technique for such application is as follows. Solutions containing one or more colorless compounds of Formulas I, X, XI, XII and XIII optionally in admixture with other color formers, in suitable solvents are microencapsulated by well-known procedures, for example, as described in U.S. Pat. Nos. 3,649,649, 3,429,827 and 4,000,087. The microcapsules are coated on the reverse side of a sheet with the aid of a suitable binder and the coated transfer sheet is then assembled in a manifold with the microcapsule coated side in contact with a receiving sheet coated with an electron-accepting substance, for example, silton clay or a phenolic resin. Application of pressure to the manifold such as that exerted by a stylus, typewriter or other form of writing or printing causes the capsules on the reverse side to rupture. The solution of the color formers released from the ruptured microcapsules flows to the receiving sheet and on contact with the acidic medium thereon forms green-gray to reddish-violet colored images of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formulas I, X, XI, XII and XIII are intimately mixed with an acidic developer of the type generally employed in thermal papers such as described in U.S. Pat. No. 3,539,375, that is, papers which produce a colored image when contacted with a heated stylus or heated type, for example, bisphenol A, heating of the mixture produces a colored image of varying shades from green-gray to reddish-violet depending on the particular compound of the invention employed. The ability of the compounds of Formulas I, X, XI, XII and XIII to form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

Further, it has been found that when the compounds of Formulas I, X, XI, XII and XIII are intimately mixed with an oxidizing agent developer of the type employed in thermal papers such as described in U.S. Pat. No. 3,447,944, that is, papers which produce a colored image when contacted with a heated stylus or heated type, for example, benzoyl peroxide, heating of the mixture produces a colored image of varying shades from green-gray to reddish-violet depending on the particular compound of the invention employed. The ability of the compounds of Formulas I, X, XI, XII and XIII to form a deep color when heated in admixture, makes them useful in thermal paper marking systems, either where an original or a duplicate copy is prepared by contacting the thermal paper with a heated stylus or heated type in any of the methods generally known in the art.

The best mode contemplated by the inventors of carrying out this invention will now be described so as to enable any person skilled in the art to which it pertains to make and use the same.

In accordance with the aforementioned process aspect of this invention the [(X)(Y)(indolyl)]methanes of Formula I which encompass both known trisubstituted methanes and the novel methanes of Formulas X, XI and XII are obtained by reacting approximately equimolar amounts of a [(X)(Y)(R-phenylsulfonyl)]methane compound of Formula II and a $1\text{-}R^9\text{-}2\text{-}R^{10}\text{-}5/6\text{-}R^{11}$-indole of Formula III wherein X, Y, R, $R^9$, $R^{10}$ and $R^{11}$ have the same respective meanings given above in relation to Formulas I, II and III. These reactions are conveniently carried out in a reaction medium, for example, a lower hydrocarbon chain alcohol, such as ethanol, or a lower hydrocarbon chain ketone, such as acetone, in the presence of an alkaline or an acidic catalyst, for example, potassium hydroxide or hydrochloric acid, at a temperature in the range of 0°–100° C. for approximately one to approximately seventy hours. The [(X)(Y)(indolyl)]methanes of Formula I thus obtained can be isolated by filtration if the product is not soluble in the reaction medium. Alternatively, the reaction mixture can be poured into water or a dilute aqueous base, for example, ammonium hydroxide and the methane isolated by filtration or extracted with an organic solvent, for example, toluene followed by evaporation of the organic solvent leaving the product as a residue. The isolated methane can be purified by conventional means such as trituration, recrystallization or reslurrying with a suitable organic liquid.

In accordance with another of the process aspects of this invention, the [(X)(Y)(1-$R^9$-2-B'O-carbonyl-5/6-$R^{11}$-indol-3-yl)]methanes of Formula VIII wherein X, Y, $R^9$, $R^{11}$ and B' each have the same respective meanings given in relation to Formula VIII are obtained by interacting a [(X)(Y)(1-$R^9$-2-carboxy-5/6-$R^{11}$-indol-3-yl)]methane with an appropriate alkylating agent, for example, dimethyl sulfate, diethyl sulfate, ethyl iodide, n-butyl bromide, n-hexadecyl bromide, benzyl bromide, benzyl chloride, and the like in an inert diluent, for example, N,N-dimethylformamide, acetone, isopropyl alchol and the like in the presence of an alkali metal hydroxide or carbonate, for example, sodium hydroxide, potassium hydroxide, sodium carbonate or potassium carbonate. The reaction is conveniently carried out at a temperature in the range of 30°–60° C. for approximately one-half to approximately ten hours. The corresponding methanes thus obtained are isolated by slowly adding the reaction mixture to a mixture of ice and water. The product which separates is then collected by filtration. The methane thus obtained can be purified, if needed, by conventional means, for example, by reslurrying in, or recrystallizing from an organic liquid.

The [(X)(Y)(R-phenylsulfonyl)]methanes of Formula II required as starting materials in the preparation of the products of Formula I are known, for example, as disclosed in U.S. Pat. No. 4,257,954, which issued on Mar. 24, 1981, in the names of Paul Joseph Schmidt and William Mo-Wei Hung. This patent is hereby incorporated by reference.

The indole compounds represented by 1-$R^9$-2-$R^{10}$-5/6-$R^{11}$-indole which are required to obtain the [(X)(Y)(1-$R^9$-2-$R^{10}$-5/6-$R^{11}$-indol-3-yl)]methanes of Formula I form an old and well-known class of compounds readily obtained by conventional processes well known in the art. The following list of compounds exemplifies indole compounds falling within the ambit of the 1-$R^9$-2-$R^{10}$-5/6-$R^{11}$-indole, which are useful in the practice of the processes of this invention for producing the aforesaid methanes of Formula I. Indole, 1-methylindole, 2-methylindole, 1,2-dimethylindole, 1-ethyl-2-methylindole, 2-phenylindole, 1-propyl-2-methylindole, 1-benzyl-2-methylindole, 1-butyl-2-methylindole, 1-octyl-2-methylindole, 2-ethyl-5-methylindole, 1-benzyl-5-fluoroindole, 1-methyl-6-nitroindole, 5-methoxy-1-butylindole, 1-allyl-2-methylindole, 1,2-dimethyl-6-nitroindole, 1-(4-chlorobenzyl)-2-methyl-5-nitroindole, 2-ethylindole, 2-ethyl-1-methylindole, 1-isopropylindole, 2-isopropylindole, 1-methyl-5-bromo-6-nitroindole, 2,5,6-trimethylindole, 1-isobutyl-2-methylindole, 6-bromo-2-methylindole, 1-hexylindole, 1-(2,5-dimethylbenzyl)-2- methylindole, 2-propylindole, 6-chloro-2-phenylindole, 1-(2-ethylhexyl)-2-methylindole, 1-(2,6-dichlorobenzyl)-2-methylindole, 1-vinyl-2-methylindole, 2-ethyl-6-methylindole, 6-fluoro-1-benzylindole, 1-(4-bromobenzyl)-2-isopropylindole, 1-(3-chlorobenzyl)-2-ethylindole, 5-chloro-1-benzylindole, 1-(2-fluorobenzyl)-2-methylindole, 5-iodo-1-(1-methylhexyl)indole, 5,6-dimethoxyindole, 1-(2-methylbenzyl)-2-methylindole, 5,6-dichloro-2-phenylindole, 1-isoamylindole, 1-[3-(2-methyl)-1-propenyl]-2-methoxyindole, indole-2-carboxylic acid, 5-chloroindole-2-carboxylic acid, 5-methoxyindole-2-carboxylic acid, 1-methylindole-2-carboxylic acid, 1-butylindole-2-carboxylic acid, 1-ethylindole-2-carboxylic acid and 1-hexadecylindole-2-carboxylic acid.

The molecular structures of the compounds of this invention were assigned on the basis of the modes of synthesis and study of their infrared and nuclear magnetic resonance spectra.

The following examples will further illustrate the invention without, however, limiting it thereto. All melting points are uncorrected.

EXAMPLE 1

With stirring, 3.0 ml of concentrated hydrochloric acid was added to a mixture of 8.0 g of [bis(4-dimethylaminophenyl)(4-methylphenylsulfonyl)]methane, 4.0 g of 85 percent 1-ethyl-2-methylindole and 150.0 ml of acetone. After stirring approximately twenty hours at ambient temperature, the resultant solution was added slowly with stirring to a solution consisting of 25.0 ml of concentrated ammonium hydroxide and one liter of water. The solid which separated was collected by filtration. The water-wet filter cake was reslurried in 150.0 ml of ethyl alcohol at reflux temperature for approximately thirty minutes. After cooling to room temperature, the solid was collected by filtration and dried to obtain 5.5 g of [bis(4-dimethylaminophenyl)(1-ethyl-2-methylindol-3-yl)]methane (Formula IV: $R^1=R^2=R^4=R^{11}=H$; $R^3=R^5=N(CH_3)_2$; $R^9=C_2H_5$; $R^{10}=CH_3$), a white-colored solid which melted at 165°–166° C. The nuclear magnetic resonance spectrum was concordant with the assigned structure. An infrared maximum appeared at 740 (C—H;s) cm$^{-1}$. A toluene solution of the product spotted on an acidic clay-coated paper or phenolic resin-coated paper slowly developed a violet-colored image.

EXAMPLE 2

To a stirred mixture {(4-dimethylaminophenyl)[4-(N-ethylbenzylamino)phenyl](4-methylphenylsulfonyl)}methane, 1.6 g of 2-methyl-5-methoxyindole and 150.0 ml of acetone, there was added 2.0 g of potassium hydroxide. The resultant mixture was stirred approximately five hours at ambient temperature and then was added slowly to stirred mixture of water and toluene. After approximately thirty minutes the stirring was stopped and the water layer was separated from the toluene layer and discarded. The toluene layer was mixed with an aqueous saturated sodium chloride solution, the layers allowed to separate and the salt water layer separated and discarded. The toluene layer was then evaporated under ambient conditions to obtain a residue which was triturated with a mixture of equal volumes of hexane and isopropyl alcohol. The solid which formed was collected by filtration and dried to obtain 1.9 g of {(4-dimethylaminophenyl)[4-(N-ethylbenzylamino)phenyl](2-methyl-5-methoxyindol-3-yl)}methane (Formula X: $R^1=R^2=R^4=R^{9'}=H$; $R^{3'}=N(CH_3)_2$; $R^5=N(C_2H_5)(CH_2C_6H_5)$; $R^{10}=CH_3$; $R^{11}=OCH_3$), a light gray-colored solid which melted at 169°–172° C. A maximum appeared in the infrared spectrum at 740 (C—H;s) cm$^{-1}$. A toluene solution of the product spotted on an acidic clay-coated paper or a phenolic resin-coated paper slowly developed a violet-colored image.

EXAMPLE 3

With stirring, 2.0 g of potassium hydroxide was added slowly to a mixture of 6.7 g of [(4-dimethylaminophenyl)(1-ethyl-2-methylindol-3-yl)(4-methylphenylsulfonyl)]methane, 2.5 g of 2-methylindole and 75.0 ml of acetone. The resulting mixture was stirred approximately twenty hours at ambient temperature and slowly added with stirring to cold water. The precipitate which formed was collected by filtration and washed three times each with 50.0 ml of hexane. The hexane-wet filter cake was dissolved in toluene. The toluene solution was extracted with water and the toluene layer containing the product was stirred with decolorizing carbon for approximately thirty minutes and the carbon removed by filtration. The toluene was removed by distillation at reduced pressure to obtain a gum-like residue. The residue was dissolved in 150.0 ml of acetone and the resulting solution was added slowly to a mixture of 800.0 ml of water, 10.0 ml of concentrated ammonium hydroxide and 50.0 ml of saturated aqueous sodium chloride solution. The solid which separated was collected by filtration, washed with water and dried in vacuo to obtain 3.9 g of [(4-dimethylaminophenyl)(1-ethyl-2-methylindol-3-yl)(2-methylindol-3-yl)]methane (Formula V: $R^1=R^2=R^8=R^9=R^{11}=H$; $R^3=N(CH_3)_2$; $R^7=R^{10}=CH_3$; $R^6=C_2H_5$), a pale brown-colored solid which melted over the range of 69°–80.5° C. An infrared maxima appeared at 745 (C—H;s) cm$^{-1}$. A toluene solution of the product spotted on an acidic clay-coated paper or phenolic resin-coated paper slowly developed a blue-red-colored image.

EXAMPLE 4

With stirring, 2.0 g of potassium hydroxide was added slowly to a mixture of 6.7 g of [(4-dimethylaminophenyl)(1-ethyl-2-methylindol-3-yl)(4-methylphenylsulfonyl)]methane, 2.4 g of indole and 75.0 ml of acetone. The resultant mixture was stirred approximately 65 hours at ambient temperature. Fifty milliliters of isopropyl alcohol was added to the reaction mixture and the resulting solution was added slowly to water. The gum-like residue which resulted was isolated by decanting the supernatant liquid. The residue was triturated with a mixture of 66.6 ml of hexane and 133.4 ml of isopropyl alcohol. The solid which formed was collected by filtration to obtain 0.4 g of a brown solid. The filtrate was added to a mixture of toluene and water. After mixing thoroughly, the layers separated and the water layer was removed. The toluene layer was washed first with water and then with saturated aqueous sodium chloride solution. The resulting toluene layer was distilled under reduced pressure to obtain a gum-like residue which was triturated with hexane. The solid which formed was collected by filtration and dried to obtain 3.6 g of [(4-dimethylaminophenyl)(1-ethyl-2-methylindol-3-yl)(indol-3-yl)]methane (Formula V: $R^1=R^2=R^8=R^9=R^{10}=R^{11}=H$; $R^3=N(CH_3)_2$; $R^6=C_2H_5$; $R^7=CH_3$), a pale brown-colored solid which melted over the range 142°–151° C. The infrared spectrum of the product had a significant maximum at 745 (C—H;s) cm$^{-1}$. A toluene solution of the product spotted on an acidic clay-coated paper or a phenolic resin-coated paper slowly developed a red-colored image.

EXAMPLE 5

To a mixture of 4.1 g of [(2-thienyl)(1-ethyl-2-methylindol-3-yl)(4-methylphenylsulfonyl)]methane, 2.0 g of 2-methylindole and 70.0 ml of acetone, there was added slowly 2.0 g of potassium hydroxide. The resulting solution was stirred approximately twenty hours at ambient temperature. The solid which formed was collected by filtration, washed with a small amount of acetone, then washed alkali-free with water and dried to obtain 1.2 g of [(2-thienyl)(1-ethyl-2-methylindol-3-yl)(2-methylindol-3-yl)]methane (Formula VII: $R^6=C_2H_5$; $R^7=R^{10}=CH_3$; $R^8=R^9=R^{11}=H$), a white-colored solid which melted at 177°–179° C. The infrared spectrum had a significant maximum at 750 (C—H;s) cm$^{-1}$. The nuclear magnetic resonance spectrum was consistent with the assigned structure. A toluene solution of the product spotted on an acid clay-coated paper or a phenolic resin-coated paper slowly developed a chocolate brown-colored image.

EXAMPLE 6

Two grams of potassium hydroxide was added slowly to a mixture of 6.3 g of [bis(4-dimethylaminophenyl)(4-methylphenylsulfonyl)]methane, 2.5 g of 2-methylindole and 75.0 ml of acetone. The resulting slurry was stirred for approximately 24 hours at ambient temperature. Fifty milliliters of isopropyl alcohol was added to the reaction mixture to effect complete solution. Slowly with stirring, the resulting solution was added to one liter of water and the solid which formed was collected by filtration. The wet filter cake was suspended in 100.0 ml of isopropyl alcohol and stirred approximately thirty minutes. The solid was collected by filtration, washed twice with 25.0 ml of isopropyl alcohol each and dried to obtain 5.1 g of [bis(4-dimethylaminophenyl)(2-methylindol-3-yl)]methane Formula IV: $R^1=R^2=R^4=R^9=R^{11}=H$; $R^3=R^5=N(CH_3)_2$; $R^{10}=CH_3$), a pale gray-colored solid which melted at 198°–202° C. A significant infrared maximum appeared at 740 (C—H;s) cm$^{-1}$. The nuclear magnetic resonance spectrum was concordant with the assigned structure. A toluene solution of the product spotted on an acid clay-coated paper or a phenolic resin-coated paper slowly developed a grape-colored image.

The following table (Table A) lists [(X)(Y)(1-$R^9$-2-$R^{10}$-5/6-$R^{11}$-indol-3-yl]methanes prepared from the interaction of a [(X)(Y)(R-phenylsulfonyl)]methane and a 1-$R^9$-2-$R^{10}$-5/6-$R^{11}$-indole in the presence of an acid or an alkaline catalyst in a manner similar to that described in Examples 1–6 above. The starting methanes listed in the second column were interacted with the indoles shown in the third column in the presence of a catalyst indicated in the fourth column in the reaction medium designated in the fifth column. The substituted methane product, obtained is listed in the sixth column with its formula number and substituents so indicated in the seventh and eighth columns, respectively and the product's appearance and melting point in the ninth and tenth columns, respectively. A significant infrared maximum is shown in the eleventh column and the results of the nuclear magnetic spectral analysis are shown in the twelth column. The substituted methanes were tested as carbonless duplicating color precursors by dissolving the product in toluene and streaking the toluene solution on an acidic clay-coated paper sheet and a phenolic resin-coated paper sheet. The colors of the images which slowly developed in this streaking test are indicated in the thirteenth column of the table. Table A has been divided into two parts, Part I contains Columns 1 through 6 and Part II contains Columns 7 through 13.

TABLE A

PART I

| Example No. | Starting Material | | Indole | Catalyst | Reaction Medium | Methane Product | |
| --- | --- | --- | --- | --- | --- | --- | --- |
| 7 | 7.5 g | [Bis(4-dimethyl-aminophenyl)(4-methylphenylsulfonyl)]methane | 2.4 g | Indole | KOH | Acetone | 4.8 g | [Bis(4-dimethylaminophenyl)(indol-3-yl)]methane |
| 8 | 8.0 g | [Bis(4-dimethyl-aminophenyl)(4-methylphenylsulfonyl)]methane | 3.5 g | 2-Methyl-indole | HCl | Acetone | 6.2 g | [Bis(4-dimethylaminophenyl)(2-methylindol-3-yl)]methane |
| 9 | 5.0 g | [(4-Dimethylamino-phenyl)(4-N—ethyl-benzylaminophenyl)]methane | 2.0 g | 2-Methyl-indole | KOH | Acetone | 3.6 g | [(4-Dimethylaminophenyl)(4-N—ethylbenzylaminophenyl)(2-methylindol-3-yl)]methane |
| 10 | 5.0 g | [(4-Dimethylamino-phenyl)(4-N—ethyl-benzylaminophenyl)(4-methylphenylsulfonyl)]methane | 1.7 g | 1-Ethyl-2-methylindole | HCl | Ethanol | 3.1 g | [(4-Dimethylaminophenyl)(4-N—ethylbenzylaminophenyl)(1-ethyl-2-methylindol-3-yl)]methane |
| 11 | 8.0 g | [Bis(4-dimethyl-aminophenyl)(4-methylphenylsulfonyl)]methane | 3.1 g | 1,2-Di-methyl-indole | HCl | Ethanol | 8.0 g | [Bis(4-dimethylaminophenyl)(1,2-dimethylindol-3-yl)]methane |
| 12 | 8.0 g | [Bis(4-dimethyl-aminophenyl)(4-methylphenylsulfonyl)methane | 4.97 g | 1-n-butyl-2-methyl-indole | HCl | Ethanol | 10.3 g | [Bis(4-dimethylaminophenyl)(1-n-butyl-2-methylindol-3-yl)]methane |
| 13 | 5.0 g | [(4-Dimethyl-aminophenyl)(4-N—ethylbenzylaminophenyl)(4- | 1.6 g | 1,2-Dimeth-ylindole | HCl | Ethanol | 4.9 g | [(4-Dimethylaminophenyl)(4-N—ethylbenzylaminophenyl)(1,2-dimethylindol-3-yl)]methane |

TABLE A-continued

| | | | | | | | |
|---|---|---|---|---|---|---|---|
| 14 | 5.0 g | methylphenylsulfonyl)]methane [(4-Dimethylaminophenyl)(4-N—ethylbenzylaminophenyl)(4-methylphenylsulfonyl)]methane | 1.2 g | Indole | KOH | Acetone | 1.2 g | [(4-Dimethylaminophenyl)(4-N—ethylbenzylaminophenyl)(indol-3-yl]methane |
| 15 | 4.7 g | [4-Methoxyphenyl)(2-ethoxy-4-diethylaminophenyl)(4-methylphenylsulfonyl)]methane | 1.6 g | 1,2-Dimethylindole | HCl | Ethanol | 1.9 g | [(4-Methoxyphenyl)(2-ethoxy-4-diethylaminophenyl)(1,2-dimethylindol-3-yl)]-methane |
| 16 | 4.7 g | [(4-Methoxyphenyl)(2-ethoxy-4-diethylaminophenyl)(4-methylphenylsulfonyl)]methane | 1.68 g | 1-Ethyl-2-methyl-indole | HCl | Ethanol | 2.4 g | [(4-Methoxyphenyl)(2-ethoxy-4-diethylaminophenyl)(1-ethyl-2-methylindol-3-yl)]methane |
| 17 | 9.1 g | [(4-Dimethylaminophenyl)(1-ethyl-2-methylindol-3-yl)(4-methylphenylsulfonyl)]methane | 3.1 g | 1,2-Dimethylindole | HCl | Ethanol | 8.1 g | [(4-Dimethylaminophenyl)(1-ethyl-2-methylindol-3-yl)(1,2-dimethylindol-3-yl)]methane |
| 18 | 9.1 g | [(4-Dimethylaminophenyl)(1-ethyl-2-methylindole-3-yl)(4-methylphenylsulfonyl)]methane | 7.0 g | 1-n-Butyl-2-methylindole | HCl | Ethanol | 9.3 g | [(4-Dimethylaminophenyl)(1-ethyl-2-methylindol-3-yl)(1-n-butyl-2-methylindol-3-yl)]methane |
| 19 | 4.1 g | [(2-Thienyl)(1-ethyl-2-methylindol-3-yl)(4-methylphenylsulfonyl)]methane | 1.2 g | Indole | HCl | Acetone | 1.98 g | [(2-Thienyl)(1-ethyl-2-methylindol-3-yl)(indol-3-yl)]methane |
| 20 | 8.1 g | [(2-Thienyl)(1-ethyl-2-methylindol-3-yl)(4-methylphenylsulfonyl)]methane | 7.0 g | 1-n-Butyl-2-methylindole | HCl | Ethanol | 10.5 g | [(2-Thienyl)(1-ethyl-2-methylindol-3-yl)(1-n-butyl-2-methylindol-3-yl)]methane |
| 21 | 8.1 g | [(2-Thienyl)(1-ethyl-2-methylindol-3-yl)(4-methylphenylsulfonyl)]methane | 3.1 g | 1,2-Dimethylindole | HCl | Ethanol | 7.9 g | [(2-Thienyl)(1-ethyl-2-methylindol-3-yl)(1,2-dimethylindol-3-yl)]-methane |
| 22 | 7.2 g | [(4-Methoxyphenyl)(4-dimethylaminophenyl)(4-methylphenylsulfonyl)]methane | 3.2 g | 1-Ethyl-2-methylindole | HCl | Ethanol | 3.9 g | [(4-Methoxyphenyl)(4-dimethylaminophenyl)(1-ethyl-2-methylindol-3-yl)]methane |
| 23 | 4.7 g | [(4-Methoxyphenyl)(4-dimethylaminophenyl)(4-methylphenylsulfonyl)]methane | 2.0 g | 2-Phenylindole | HCl | Ethanol | 5.6 g | [(4-Methoxyphenyl)(4-dimethylaminophenyl)(2-phenylindol-3-yl)]-methane |
| 24 | 7.3 g | [(Phenyl)(4-dimethylaminophenyl)(4-methylphenylsulfonyl)]methane | 3.0 g | 1,2-Dimethylindole | HCl | Ethanol | 4.5 g | [(Phenyl)(4-dimethylaminophenyl)(1,2-dimethylindol-3-yl)]-methane |
| 25 | 7.3 g | [(Phenyl)(4-dimethylaminophenyl)(4-methylphenylsulfonyl)]methane | 3.55 g | 1-Ethyl-2-methylindole | HCl | Ethanol | 5.68 g | [(Phenyl)(4-dimethylaminophenyl)(1-ethyl-2-methylindol-3-yl)]-methane |
| 26 | 8.8 g | [(Phenyl)(2-ethoxy-4-diethylaminophenyl)(4-methylphenylsulfonyl)]-methane | 3.6 g | 1-Ethyl-2-methylindole | HCl | Ethanol | 10.0 g | [(Phenyl)(2-ethoxy-4-diethylaminophenyl)(1-ethyl-2-methylindol-3-yl)]methane |
| 27 | 9.4 g | [(2-Methoxyphenyl)(2-ethoxy-4-diethylaminophenyl)(4-methylphenylsulfonyl)]methane | 3.2 g | 1-Ethyl-2-methylindole | HCl | Ethanol | 5.3 g | [(2-Methoxyphenyl)(2-ethoxy-4-diethylaminophenyl)(1-ethyl-2-methylindol-3-yl)]methane |
| 28 | 20.5 g | [(4-Nitrophenyl)(4-dimethylaminophenyl)(4-methylphenylsulfonyl)]-methane | 9.45 g | 1-Ethyl-2-methylindole | HCl | Ethanol | 7.31 g | [(4-Nitrophenyl)(4-dimethylaminophenyl)(1-ethyl-2-methylindol-3-yl)]methane |

TABLE A-continued

| | | | | | | | |
|---|---|---|---|---|---|---|---|
| 29 | 8.38 g | [(4-Nitrophenyl)(2-ethoxy-4-diethylaminophenyl)(4-methylphenylsulfonyl)]methane | 3.25 g | 1-Ethyl-2-methyl-indole | HCl | Ethanol | 5.86 g | [(4-Nitrophenyl)(2-ethoxy-4-diethylaminophenyl)(1-ethyl-2-methylindol-3-yl)]methane |
| 30 | 8.2 g | [(3-Nitrophenyl)(4-dimethylaminophenyl)(4-methylphenylsulfonyl)]methane | 3.56 g | 1-Ethyl-2-methyl-indole | HCl | Ethanol | 1.89 g | [(3-Nitrophenyl)(4-dimethylaminophenyl)(1-ethyl-2-methylindol-3-yl)]methane |
| 31 | 9.6 g | [(3-Nitrophenyl)(2-ethoxy-4-diethylaminophenyl)(4-methylphenylsulfonyl)]methane | 3.56 g | 1-Ethyl-2-methyl-indole | HCl | Ethanol | 6.91 g | [(3-Nitrophenyl)(2-ethoxy-4-diethylaminophenyl)(1-ethyl-2-methylindol-3-yl)]- |
| 32 | 4.6 g | [(4-Dimethylaminophenyl)(9-julolidinyl)(4-methylphenylsulfonyl)]methane | 1.62 g | 1-Ethyl-2-methyl-indole | HCl | Ethanol | 0.15 g | [(4-Dimethylaminophenyl)(9-julolidinyl)(1-ethyl-2-methylindol-3-yl)]methane |
| 33 | 11.2 g | [(4-Methoxyphenyl)(2-ethoxy-4-diethylaminophenyl)(4-methylphenylsulfonyl)]methane | 6.6 g | 1-n-Butyl-2-methyl-indole | HCl | Ethanol | 2.3 g | [(4-Methoxyphenyl)(2-ethoxy-4-diethylaminophenyl)(1-n-butyl-2-methylindol-3-yl)]methane |
| 34 | 17.9 g | [(3-Nitrophenyl)(2-ethoxy-4-diethylaminophenyl)(4-methylphenylsulfonyl)]methane | 10.1 g | 1-n-Butyl-2-methyl-indole | HCl | Ethanol | 2.6 g | [(3-Nitrophenyl)(2-ethoxy-4-diethylaminophenyl)(1-n-butyl-2-methylindol-3-yl)]methane |
| 35 | 17.9 g | [(3-Nitrophenyl)(2-ethoxy-4-diethylaminophenyl)(4-methylphenylsulfonyl)]methane | 10.0 g | 1-Allyl-2-methyl-indole | HCl | Ethanol | 9.4 g | [(3-Nitrophenyl)(2-ethoxy-4-diethylaminophenyl)(1-allyl-2-methylindol-3-yl)]methane |
| 36 | 7.8 g | [(4-Methoxyphenyl)(4-dimethylaminophenyl)(4-methylphenylsulfonyl)]methane | 3.9 g | 1-Methyl-indol-2-carboxylic acid | HCl | Ethanol | 2.1 g | [(4-Methoxyphenyl)(4-dimethylaminophenyl)(1-methyl-2-carboxyindol-3-yl)]methane |
| 37 | 9.9 g | [(Phenyl)(4-dimethylaminophenyl)(4-methylphenylsulfonyl)]methane | 5.6 g | 1-n-Butyl-2-methyl-indole | HCl | Ethanol | 2.45 g | [(Phenyl)(4-dimethylaminophenyl)(1-n-butyl-2-methylindol-3-yl)]methane |

PART II

| Example No. | Formula No. | Substituents | Product Color | Melting Point (C.°) | IR cm$^{-1}$ | NMR | Developed Color |
|---|---|---|---|---|---|---|---|
| 7 | IV | $R^1=R^2=R^4=R^{10}=R^{11}=H$; $R^3=R^5=N(CH_3)_2$ | Pale Tan | 239–240 | 740(C—H;s) | Consistent | Grape on clay and resin |
| 8 | IV | $R^1=R^2=R^4=R^9=R^{11}=H$; $R^3=R^5=N(CH_3)_2$; $R^{10}=CH_3$ | Pale Tan | 148–151 | 740(C—H;s) | Consistent | Grape on clay and resin |
| 9 | X | $R^1=R^2R^4=R^{9'}=R^{11}=H$; $R^3=N(CH_3)_2$; $R^5=N(C_2H_5)(CH_2—C_6H_5)$; $R^{10}=CH_3$ | Brown | Tar | 740(C—H;s) | Consistent | Violet on clay and resin |
| 10 | X | $R^1=R^2=R^4=R^{11}=H$; $R^3=N(CH_3)_2$; $R^5=N(C_2H_5)—(CH_2C_6H_5)$; $R^{9'}=C_2H_5$; $R^{10}=CH_3$ | Brown | Gum | 740(C—H;s) | Consistent | Purple on clay and resin |
| 11 | IV | $R^1=R^2R^4=R^{11}=H$; $R^3=R^5=N(CH_3)_2$; $R^9=R^{10}=CH_3$ | Pale Blue | 177–184 | 740(C—H; s) | Consistent | Violet on clay and resin |
| 12 | X | $R^1=R^2=R^4=R^{11}=H$; $R^3=R^5=N(CH_3)_2$; $R^9=n-C_4H_9$; $R^{10}=CH_3$ | Purple | Gum | 740(C—H;s) | Consistent | Violet on clay and resin |
| 13 | X | $R^1=R^2=R^4=R^{11}=H$; $R^{3'}=N(CH_3)_2$; $R^5=N(C_2H_5)—(CH_2C_6H_5)$; $R^{9'}=R^{10}=CH_3$ | Pale Green-Gray | 58–60 | 730(C—H;s) | Consistent | Violet on clay |
| 14 | X | $R^1=R^2=R^4=R^{9'}=R^{10}=R^{11}=H$; $R^{3'}=N(CH_3)_2$; $R^5=N(C_2H_5)—(CHC_6H_5)$ | Blue | Tar | 742(C=H;s) | Consistent | Grape on clay |
| 15 | IV | $R^1=R^2=R^{11}=H$; $R^3=OCH_3$; $R^4=OC_2H_5$; $R^5=N(C_2H_5)_2$; $R^9=R^{10}=CH_3$ | Pale Green | Gummy Oil | 730(C—H;s) | Consistent | Blue on clay |
| 16 | X | $R^1=R^2=R^{11}=H$; $R^3=OCH_3$; $R^4=OC_2H_5$; $R^5=N(C_2H_5)_2$; $R^{9'}=C_2H_5$; $R^{10}=CH_3$ | Pale Green | Gum | 735(C—H;s) | Consistent | Chocolate on clay Blue on resin |

TABLE A-continued

| | | | | | | | |
|---|---|---|---|---|---|---|---|
| 17 | V | $R^1=R^2=R^8=R^{11}=H$; $R^3=N(CH_3)_2$; $R^6=C_2H_5$; $R^7=R^9=R^{10}=CH_3$ | Pale Pink | 167-170.5 | 743(C—H;s) | Consistent | Red on clay |
| 18 | V | $R^1=R^2=R^8=R^{11}=H$; $R^3=N(CH_3)_2$; $R^6=C_2H_5$; $R^7=R^{10}=CH_3$; $R^9=$ n-$C_4H_9$ | Magenta | Gummy Oil | 740(C—H;s) | — | Blue-Red on clay |
| 19 | VII | $R^6=C_2H_5$; $R^7=CH_3$; $R^8=R^9=R^{10}=R^{11}=H$ | Brown | Tar | 745(C—H;s) | — | Brown on clay |
| 20 | VII | $R^6=C_2H_5$; $R^7=R^{10}=CH_3$; $R^8=R^{11}=H$; $R^9=$n-$C_4H_9$ | Brown | Gum | 740(C—H;s) | — | Brown on clay |
| 21 | VII | $R^6C_2H_5$; $R^7=R^9=R^{10}=CH_3$; $R^8=R^{11}=H$ | Pale Pink | 167-170 | 743(C—H;s) | Consistent | Brown on clay |
| 22 | X | $R^1=R^2=R^4=R^{11}=H$; $R^3=OCH_3$; $R^5=N(CH_3)_2$; $R^{9'}=C_2H_5$; $R^{10}=CH_3$ | White | 145-146 | 742(C—H;s) | Consistent | Blue on Grape on clay |
| 23 | III | $R^1=R^2=R^4=R^9=R^{11}=H$; $R^3=OCH_3$; $R^5=N(CH_3)_2$; $R^{10}=C_6H_5$ | Pale Pink | 107-108 | 750(C—H;s) | Consistent | Blue on resin Pink-Brown on clay |
| 24 | III | $R^1=R^2=R^3=R^4=R^{11}=H$; $R^5=N(CH_3)_2$; $R^9=R^{10}=CH_3$ | Pale Purple | 149-150 | 745(C—H;s) | Consistent | Blue on clay |
| 25 | X | $R^1=R^2=R^{3'}=R^4=R^{11}=H$; $R^5=N(CH_3)_2$; $R^{9'}=C_2H_5$; $R^{10}=CH_3$ | Cream | 131-132 | 755(C—H;s) | Consistent | Blue on clay |
| 26 | X | $R^1=R^2=R^{3'}=H$; $R^4=OC_2H_5$; $R^5=N(CH_3)_2$; $R^{9'}=C_2H_5$; $R^{10}=CH_3$ | Light Tan | 100-102 | 750(C—H;s) | Consistent | Blue on Green-Brown on clay |
| 27 | X | $R^1=R^2=R^{11}=H$; $R^{3'}=OCH_3$; $R^4=OC_2H_5$; $R^5=N(CH_3)_2$; $R^{9'}=C_2H_5$; $R^{10}=CH_3$ | White | 112-113 | 750(C—H;s) | Consistent | Blue on resin Tan on clay |
| 28 | X | $R^1=R^2=R^4=R^{11}=H$; $R^{3'}=NO_2$; $R^5N(CH_3)_2$; $R^{9'}=C_2H_5$; $R^{10}=CH_3$ | Yellow | 168-170 | 755(C—H;s) | Consistent | Blue-Green on clay |
| 29 | X | $R^1=R^2=R^{11}=H$; $R^{3'}=NO_2$; $R^4=OC_2H_5$; $R^5=N(C_2H_5)$; $R^{9'}=C_2H_5$; $R^{10}=CH_3$ | Yellow | 116-118 | 760(C—H;s) | Consistent | Blue-Green on resin Yellow-Green on clay |
| 30 | X | $R^1=R^{3'}=R^4=R^{11}=H$; $R^2=NO_2$; $R^5=N(CH_3)_2$; $R^{9'}=C_2H_5$; $R^{10}=CH_3$ | Yellow | 138-139 | 755(C=H;s) | Consistent | Blue-Green on resin Blue on clay |
| 31 | X | $R^1=R^{3'}=R^{11}=H$; $R^2=NO_2$; $R^4=OC_2H_5$; $R^5=N(C_2H_5)_2$; $R^{9'}=C_2H_5$; $R^{10}=CH_3$ | Yellow | 123-124 | 755(C—H;s) | Consistent | Blue on resin Blue-Green on clay |
| 32 | VI | $R^1=R^2=R^{11}=H$; $R^9=C_2H_5$; $R^{10}=CH_3$ | Pale Blue | 119-120 | 750(C—H;s) | Consistent | Blue on resin Blue on clay |
| 33 | X | $R^1=R^2=R^{11}=H$; $R^{3'}=OCH_8$; $R^4=OC_2H_5$; $R^5=N(C_2H_5)$; $R^{9'}=$n-$C_4H_9$; $R^{10}=CH_3$ | Blue | Oil | 750(C—H;s) | Consistent | Brown on clay Gray on resin |
| 34 | X | $R^1=R^{3'}=R^{11}=H$; $R^2=NO_2$; $R^4=OC_2H_5$; $R^5=N(C_2H_5)_2$; $R^{9'}=$n-$C_4H_9$; $R^{10}=CH_3$ | Green | Oil | 750(C—H;s) | Consistent | Gray-Green on clay Blue-Green on resin |
| 35 | X | $R^1=R^{3'}=R^{11}=H$; $R^2=NO_2$; $R^4=OC_2H_5$; $R^5=N(C_2H_5)_2$; $R^{9'}=CH_2CHCH_2$; $R^{10}=CH_3$ | Yellow | 113-114 | 760(C—H;s) | Consistent | Green-Gray on clay Gray on resin |
| 36 | XI | $R^1=R^2=R^4=R^{11}=B''=H$; $R^3=OCH_3$; $R^5=N(CH_3)_2$; $R^9=CH_3$ | White | 195-197 | 760(C—H;s) | Consistent | Blue-Purple on clay Red-Purple on resin |
| 37 | X | $R^1=R^2=R^3=R^4=R^{11}=H$; $R^5=N(CH_3)_2$; $R^{9'}=$n-$C_4H_9$; $R^{10}=CH_3$ | Green | Tar | 750(C—H;s) | Consistent | Blue-Purple on clay Blue on resin |

EXAMPLE 38

With stirring a mixture of 325.0 ml of ethanol, 47.5 g of [(phenyl)(4-dimethylaminophenyl)(4-methylphenylsulfonyl)]methane, 25.0 ml of 1-methylindol-2-carboxylic acid and 13.0 ml of concentrated hydrochloric acid was heated at reflux temperature for approximately twenty-two hours. The resultant solution was poured slowly into approximately 300.0 ml of cold water. The resulting suspension was extracted with approximately 500.0 ml of toluene. The toluene layer was separated and washed consecutively with water and saturated sodium chloride solution. The toluene layer was stirred for approximately one hour with decolorizing charcoal and filtered to remove the charcoal. The toluene was removed by evaporation leaving a dark blue-purple solid. The solid was suspended in ethanol, heated for approximately one hour and cooled to ambient temperature. The solid was collected by filtration, washed with isopropanol and dried to obtain 19.0 g of a mixture of starting methane and [(phenyl)(4-dimethylaminophenyl)(1-methyl-2-carboxyindol-3-yl)]methane as determined by nuclear magnetic resonance spectroscopy. The resulting solid was suspended in approximately 300.0 ml of toluene for approximately one hour and the solid collected by filtration. The toluene-wet solid was reslurried in approximately 100.0 ml of toluene at a temperature of approximately 60° C. for approximately one hour. After cooling the slurry to approximately 40° C., the solid was collected by filtration and dried to obtain 2.47 g of [(phenyl)(4-dimethylaminophenyl)(1-methyl-2-carboxyindol-3-yl)]methane (Formula XI: $R^1=R^2=R^3=R^4=R^{11}=B''=H$; $R^5=N(CH_3)_2$; $R^9=CH_3$), a cream-colored solid which melted at 214°–215° C. A significant infrared maximum appeared at 760 (C—H;s) cm$^{-1}$. The nuclear magnetic resonance spectrum was concordant with the assigned structure. A toluene solution of the product spotted on an acidic clay-coated paper slowly developed a medium blue-colored image and spotted on a phenolic resin-coated paper slowly developed a dark blue-colored image.

EXAMPLE 39

In 50.0 ml of N,N-dimethylformamide, 5.0 g of [(phenyl)(4-dimethylaminophenyl)(1-methyl-2-carboxyindol-3-yl)]methane prepared as described in Example 38 above, was dissolved with stirring. Slowly, 3.0 g of potassium carbonate was added to the solution and stirring was continued at approximately 45° C. for a period of fifteen minutes to effect solution. To the solution 5.0 ml of diethyl sulfate was added and the resulting reaction mixture was maintained at approximately 45° C. for approximately three hours. The resulting solution was cooled to approximately 30° C. and slowly poured with stirring into 200.0 ml of a mixture of ice and water. The separated solid was collected by filtration, washed with water, and allowed to dry on the filter. The dried filter cake was reslurried twice in ethanol, each time for approximately one hour. The solid was collected by filtration and dried to obtain 3.44 g of white solid. The solid was suspended with stirring in approximately 200.0 ml of hot isopropanol for approximately one hour. After cooling the slurry to ambient temperature the solid was collected by filtration and dried to obtain 1.11 g of the starting methane. The filtrate was concentrated by evaporation and the separated solid was collected by filtration and dried to obtain 1.27 g of [(phenyl)(4-dimethylaminophenyl)(1-methyl-2-ethoxycarbonylindol-3-yl]methane (Formula XI: $R^1=R^2=R^3=R^4=R^{11}=H$; $R^5=N(CH_3)_2$; $R^9=CH_3$; $B''=C_2H_5$), a white solid which melted at 145°–146° C. The infrared spectrum showed a significant maximum at 760 (C—H;s) cm$^{-1}$ and the nuclear magnetic resonance spectrum was concordant with the assigned structure. A toluene solution of the product spotted on an acidic clay-coated paper slowly developed a blue-gray-colored image.

EXAMPLE 40

Following a procedure similar to that described above in Example 39, 1.5 g of [(4-methoxyphenyl)(4-dimethylaminophenyl)(1-methyl-2-carboxyindol-3-yl)]methane prepared in Example 36 above, 1.0 g of potassium carbonate and 1.0 ml of dimethylsulfate were interacted in 25.0 ml of N,N-dimethylformamide at approximately 45° C. for a period of two hours to obtain 0.94 g of [(4-methoxyphenyl)(4-dimethylaminophenyl)(1-methyl-2-methoxycarbonylindol-3-yl)]methane (Formula XI: $R^1=R^2=R^4=R^{11}=H$; $R^5=N(CH_3)_2$; $R^9=B''=CH_3$), a white solid which melted at 157°–160° C. The infrared spectrum showed a significant maximum at 755 (C—H;s) cm$^{-1}$ and the nuclear magnetic resonance spectrum was consistent with the assigned structure. A toluene solution of the product spotted on an acidic clay-coated paper slowly developed a magenta-colored image and on a phenolic resin-coated paper slowly developed a pale purple-colored image.

EXAMPLE 41

With stirring 5.0 g of [(phenyl)(4-dimethylaminophenyl)(1-methyl-2-carboxyindol-3-yl)]methane prepared in Example 36 above was dissolved in 50.0 ml of N,N-dimethylformamide. Slowly, 3.0 g of potassium carbonate was added to the solution and the resulting mixture was maintained at approximately 45° C. for a period of fifteen minutes to effect solution. With stirring, 4.9 g of 1-bromohexadecane was added to the solution. The reaction solution was maintained at approximately 45° C. for approximately four hours. The temperature of the solution was increased to approximately 70° C. and an additional 4.9 g of 1-bromohexadecane was added. The resulting solution was maintained at reflux for approximately eighteen hours. After cooling to ambient temperature, the solution was poured slowly with stirring into approximately 200.0 g of a mixture of ice and water. The resulting suspension of a tar-like solid in water was extracted with toluene. After the toluene layer was separated from the water layer, it was washed first with fresh water and then with water saturated with sodium chloride. The separated toluene layer was evaporated to dryness to obtain a yellow solid. The yellow solid was reslurried in hexane. The solid was collected by filtration and dried to obtain 1.65 g of starting methane. The filtrate was evaporated to obtain a gold-colored oil. After sitting for approximately one week, the gold-colored oil had partially crystallized turning a tan-brown color. The tan-brown solid was stirred with hexane at ambient temperature and the solid collected by filtration and dried to obtain 1.75 g of solid. This solid was pasted with hexane and the resulting paste was filtered, saving the filtrate. The filter cake was washed with a small amount of hexane, the wash being saved, and the solid dried to obtain 0.12 g of [(phenyl)(4-dimethylaminophenyl)(1-methyl-2-hexadecanoxycarbonylindol-3-yl)]methane (Formula XI: $R^1=R^2=R^3=R^4=R^{11}=H$; $R^5=N(CH_3)_2$; $R^9=CH_3$;

$B''=C_{16}H_{33}$), a white-colored solid which melted at 51°-52° C. A significant infrared maximum appeared at 755 (C—H;s) cm$^{-1}$ and the nuclear magnetic resonance spectrum was consistent with the assigned structure. A toluene solution of the product spotted on an acid clay-coated paper slowly developed a blue-purple-colored image. The solid which formed in the filtrate from above was collected by filtration, discarding the filtrate. The filter cake was washed with a small amount of hexane, saving the wash filtrate, and dried to obtain an additional 0.21 g of [(phenyl)(dimethylaminophenyl)(1-methyl-2-hexadecanoxycarbonylindol-3-yl)]methane. The two hexane washes were combined and evaporated to obtain an additional 0.46 g of [(phenyl)(4-dimethylaminophenyl)(1-methyl-2-hexadecanoxycarbonylindol-3-yl)]methane.

EXAMPLE 42

Proceeding in a manner similar to that described in Example 2 above, 20.5 g of [(phenyl)(4-dimethylaminophenyl)(4-methylphenylsulfonyl)]methane was interacted with 10.0 g of indole-2-carboxylic acid in the presence of 5.6 ml of concentrated hydrochloric acid in 140.0 ml of ethanol to obtain 3.34 g of [(phenyl)(4-dimethylaminophenyl)(2-carboxyindol-3-yl)]methane (Formula XI: $R^1=R^2=R^3=R^4=R^{11}=B''=H$; $R^5=N(CH_3)_2$), a blue solid which melted at 213°-215° C. The nuclear magnetic resonance spectrum was consistent with the assigned structure. A toluene solution of the product spotted on an acid clay-coated paper slowly developed a purple-colored image and on a phenolic resin-coated paper slowly developed a dark blue-colored image.

EXAMPLE 43

In a manner similar to that described in Example 39 above, 3.34 g of [(phenyl)(4-dimethylaminophenyl)(2-carboxyindol-3-yl)]methane prepared in Example 42 above was interacted with 2.0 g of potassium carbonate and 3.5 ml of diethyl sulfate in 33.4 ml of N,N-dimethylformamide at approximately 45° C. for approximately three hours to obtain 2.47 g of [(phenyl)(4-dimethylaminophenyl)(2-ethoxycarbonylindol-3-yl)]methane (Formula XI: $R^1=R^2=R^3=R^4=R^9=R^{11}=H$; $R^5=N(CH_3)_2$; $B''=C_2H_5$), a pale pink-colored solid which melted at 72°-78° C. The infrared spectrum had a maximum which appeared at 760 (C—H;s) cm$^{-1}$ and the nuclear magnetic resonance was consistent. A toluene solution of the product spotted on an acidic clay-coated paper slowly developed a pale pink-colored image and on a phenolic resin-coated paper slowly developed a pale pink-colored image.

It is contemplated that by following procedures similar to those described in the foregoing examples but employing the appropriate [(2-$R^1$-3-$R^2$-4-$R^3$-phenyl)(2-$R^4$-4-$R^5$-phenyl)(R-phenylsulfonyl))]methane and the appropriate 1-$R^9$-2-$R^{10}$-5/6-$R^{11}$-indole of Formula III, there will be obtained the [(2-$R^1$-3-$R^2$-4-$R^3$-phenyl)(2-$R^4$-4-$R^5$-phenyl)(1-$R^9$-2-$R^{10}$-5/6-$R^{11}$-indole-3-yl)]methanes of Formula IV, Examples 44-60, presented in Table B hereinbelow.

TABLE B

METHANES OF FORMULA IV

| Example | R | $R^1$ | $R^2$ | $R^3$ | $R^4$ | $R^5$ | $R^9$ | $R^{10}$ | $R^{11}$ |
|---|---|---|---|---|---|---|---|---|---|
| 44 | 4-$CH_3$ | $N(CH_3)_2$ | H | $N(CH_3)_2$ | Cl | Cl | $CH_2C_6H_5$ | $CH_3$ | H |
| 45 | 4-Cl | H | H | N(n-$C_3H_7)_2$ | H | $CH_3O$ | n-$C_8H_{17}$ | $CH_3$ | H |
| 46 | 2-$NO_2$ | n-$C_3H_7$ | H | n-$C_3H_7$ | $C_2H_5O$ | H | H | $C_2H_5$ | $CH_3$ |
| 47 | H | n-$C_4H_9O$ | H | $N(C_2H_5)_2$ | $CH_3O$ | $CH_3O$ | $CH_2C_6H_5$ | H | F |
| 48 | 4-$CH_3$ | $C_2H_5O$ | H | Cl | H | i-$C_3H_7$ | $CH_3$ | H | $NO_2$ |
| 49 | 3,4-$(Cl)_2$ | $N(C_2H_5)_2$ | H | $N(C_2H_5)_2$ | $CH_3O$ | $N(C_2H_5)_2$ | $CH_3$ | $CH_3$ | $NO_2$ |
| 50 | 4-I | Cl | H | N(i-$C_3H_7)_2$ | H | $N(CH_3)$—$(CH_2C_6H_5)$ | H | $C_2H_5$ | N |
| 51 | 4-$CH_3O$ | I | H | N(n-$C_4H_9$)—$(CH_2C_6H_5)$ | Br | H | 4-$ClC_6$—$H_4CH_2$ | $CH_3$ | $NO_2$ |
| 52 | 3-$NO_2$ | $CH_3$ | H | $N(C_2H_5)_2$ | n-$C_3H_7$ | H | $CH_3$ | $C_2H_5$ | H |
| 53 | H | H | H | N(n-$C_3H_7$)—$(CH_2C_6H_5)$ | $CH_3$ | $N(CH_3)_2$ | i-$C_3H_7$ | H | H |
| 54 | 4-Br | n-$C_3H_7O$ | H | n-$C_3H_7O$ | $CH_3O$ | H | H | i-$C_3H_7$ | H |
| 55 | 4-Cl—3$NO_2$ | H | H | N(i-$C_4H_9$)—$(CH_2C_6H_5)$ | H | $C_2H_5O$ | $CH_3$ | H | Br,$NO_2$ |
| 56 | 4-$CH_3$ | N(n-$CH_4H_9)_2$ | H | N(n-$C_4H_9)_2$ | $CH_3O$ | H | H | $CH_3$ | $(CH_3)_2$ |
| 57 | H | H | H | N(i-$C_3H_7$)—$(CH_2C_6H_5)$ | H | $N(CH_3)_2$ | i-$C_4H_9$ | $CH_3$ | H |
| 58 | 4-F | H | $NO_2$ | H | $N(CH_3)_2$ | $N(CH_3)_2$ | H | $CH_3$ | Br |
| 59 | 4-$CH_3$ | $N(CH_3)_2$ | H | $N(CH_3)_2$ | H | $CH_3$ | n-$C_6H_{13}$ | H | H |
| 60 | 4-$CH_3$—CONH | $CH_3O$ | H | $CH_3O$ | H | $N(C_2H_5)_2$ | 2,5-$(CH_3)_2$—$C_6H_3CH_2$ | $CH_3$ | H |
| 61 | H | $N(CH_3)_2$ | H | $N(CH_3)_2$ | $CH_3O$ | $N(C_2H_5)_2$ | H | COOH | 5-Cl |
| 62 | 4-$CH_3$ | $N(C_2H_5)_2$ | H | $N(C_2H_5)_2$ | $C_2H_5O$ | $N(C_2H_5)_2$ | H | COOH | 5-$CH_3O$ |

It is contemplated that by following procedures similar to those described in the foregoing examples but employing the appropriate [(2-$R^1$-3-$R^2$-4-$R^3$-phenyl)(1-$R^6$-2-$R^7$-5/6-$R^8$-indol-3-yl)(R-phenylsulfonyl)]methane and the appropriate 1-$R^9$-2-$R^{10}$-5/6-$R^{11}$-indole of Formula III, there will be obtained the [(2-$R^1$-3-$R^2$-4-$R^3$-phenyl)(1-$R^6$-2-$R^7$-5/6-$R^8$-indol-3-yl)(1-$R^9$-2-$R^{10}$-5/6-$R^{11}$-indol-3-yl)]methanes of Formula V, Examples 63-74, presented in Table C hereinbelow.

TABLE C

METHANES OF FORMULA V

| Example | R | $R^1$ | $R^2$ | $R^3$ | $R^6$ | $R^7$ | $R^8$ | $R^9$ | $R^{10}$ | $R^{11}$ |
|---|---|---|---|---|---|---|---|---|---|---|
| 63 | 4-Br | $CH_3O$ | H | $N(CH_3)_2$ | 2-$(C_2H_5)$—$(C_6H_5CH_2)$ | $CH_3$ | H | H | $C_2H_5$ | H |

TABLE C-continued

| | | | | METHANES OF FORMULA V | | | | | | |
|---|---|---|---|---|---|---|---|---|---|---|
| Example | R | $R^1$ | $R^2$ | $R^3$ | $R^6$ | $R^7$ | $R^8$ | $R^9$ | $R^{10}$ | $R^{11}$ |
| 64 | 2,4-$(CH_3)_2$ | Cl | H | $N(CH_3)_2$ | 4-$ClC_6H_4CH_2$ | $CH_3$ | 5-$NO_2$ | $CH_3$ | $C_2H_5$ | H |
| 65 | 2-$NO_2$ | $CH_3$ | $NO_2$ | H | n-$C_8H_{17}$ | $CH_3$ | H | $CH_3$ | H | 5-Br,6-$NO_2$ |
| 66 | 3,4-$(Cl)_2$ | H | H | i-$C_3H_7$ | $CH_3$ | H | 5-Br—6-$NO_2$ | H | $CH_3$ | 5,6-$(CH_3)_2$ |
| 67 | 4-F | $CH_3O$ | H | $CH_3O$ | 2-$CH_3C_6H_4CH_2$ | $CH_3$ | H | i-$C_4H_9$ | $CH_3$ | H |
| 68 | 4-$CH_3O$ | $CH_3$ | H | $N(CH_3)(C_65CH_2)$ | H | $C_2H_5$ | 6-$CH_3$ | n-$C_6H_{13}$ | H | H |
| 69 | 3-$NO_2$ | Br | H | $NO_2$ | i-$C_4H_9$ | $CH_3$ | H | 2,5-$(CH_3)_2$—$C_6H_3CH_2$ | $CH_3$ | H |
| 70 | 4-$CH_3CONH$ | H | H | $C_2H_5O$ | 1-$(CH_3)$-$(C_6H_{12})$ | H | 5-I | H | $C_2H_5$ | 6-Cl |
| 71 | 4-Cl | H | H | $N(CH_3)(C_6H_5CH_2)$ | H | i-$C_3H_7$ | H | H | COOH | 5-Cl |
| 72 | H | $C_2H_5O$ | H | H | $C_2H_4$ | $CH_3$ | H | H | COOH | 5-$CH_3O$ |
| 73 | 2,5-$(CH_3)_2$ | H | H | Cl | i-$C_5H_{11}$ | H | 5-$CH_3O$ | $CH_3$ | COOH | H |
| 74 | H | $N(CH_3)_2$ | H | $N(CH_3)_2$ | $CH_3$ | $C_6H_5$ | H | H | H | 5,6-$(CH_3O)_2$ |

It is contemplated that by following procedures similar to those described in the foregoing examples but employing the appropriate [(2-$R^1$-3-$R^2$-4-$R^3$-phenyl)(9-julolidinyl)(R-phenylsulfonyl)]methane and the appropriate 1-$R^9$-2-$R^{10}$-5/6-$R^{11}$-indole, there will be obtained the [(2-$R^1$-3-$R^2$-4-$R^3$-phenyl)(9-julolidinyl)(1-$R^9$-2-$R^{10}$-5/6-$R^{11}$-indol-3-yl)]methanes of Formula VI, Examples 75–84, presented in Table D hereinbelow.

TABLE D

| | | | | METHANES OF FORMULA VI | | | |
|---|---|---|---|---|---|---|---|
| Example | R | $R^1$ | $R^2$ | $R^3$ | $R^9$ | $R^{10}$ | $R^{11}$ |
| 75 | 2,5-$(CH_3)_2$ | Cl | H | $N(CH_3)_2$ | H | $C_6H_5$ | 5,6-$(Cl)_2$ |
| 76 | H | H | H | Cl | i-$C_5H_{11}$ | H | H |
| 77 | 4-Cl | $N(CH_3)_2$ | H | $N(CH_3)_2$ | 2-$FC_6H_4CH_2$ | $CH_3$ | H |
| 78 | 2-$NO_2$ | $C_2H_5O$ | H | $N(CH_3)_2$ | 3-(2-$CH_3$)-1-$C_3H_5$ | $CH_3$ | H |
| 79 | 3,4-$(Cl)_2$ | $CH_3$ | H | $N(CH_3)_2$ | H | H | 5,6-$(CH_3O)_2$ |
| 80 | H | H | H | $N(C_2H_5)(C_6H_5CH_2)$ | H | COOH | H |
| 81 | 4-$CH_3CONH$ | n-$C_4H_9O$ | H | $N(n-C_4H_9)_2$ | H | COOH | Cl |
| 82 | H | H | $NO_2$ | H | $CH_3$ | COOH | H |
| 83 | 4-Br | $CH_3$ | H | $NO_2$ | H | COOH | 5-$CH_3O$ |
| 84 | 4-$CH_3$ | Br | H | Br | n-$C_{12}H_{25}$ | $CH_3$ | H |

It is contemplated that by following procedures similar to those described in the foregoing examples but employing the appropriate [(2-thieny)(1-$R^6$-2-$R^7$-5/6-$R^8$-indol-3-yl)(R-phenylsulfonyl)]methane and the appropriate 1-$R^9$-2-$R^{10}$-5/6-$R^{11}$-indole, there will be obtained the [(2-thienyl)(1-$R^6$-2-$R^7$-5/6-indol-3-yl)(1-$R^9$-2-$R^{10}$-5/6-$R^{11}$-indol-3-yl)]methanes of Formula VII, Examples 85–95, presented in Table E hereinbelow.

TABLE E

| | | METHANES OF FORMULA VII | | | | | |
|---|---|---|---|---|---|---|---|
| Example | R | $R^6$ | $R^7$ | $R^8$ | $R^9$ | $R^{10}$ | $R^{11}$ |
| 85 | 2-$NO_2$ | $CH_3$ | $CH_3$ | H | $C_2H_4$ | $CH_3$ | H |
| 86 | 4-Br | H | H | 5-$CH_3O$ | $CH_3$ | $CH_3$ | 6-$NO_2$ |
| 87 | 4-$CH_3CONH$ | H | $C_6H_5$ | H | i-$C_4H_9$ | $CH_3$ | H |
| 88 | 2,4-$(CH_3)_2$ | H | $C_2H_5$ | H | H | COOH | 5-$CH_3O$ |
| 89 | H | $C_2H_4$ | $CH_3$ | H | n-$C_{10}H_{13}$ | $CH_3$ | H |
| 90 | 4-$C_2H_5$ | H | $CH_3$ | 6-Br | H | $CH_3$ | 6-Br |
| 91 | 4-$NO_2$ | i-$C_3H_7$ | H | H | $C_6H_5CH_2$ | H | 6-F |
| 92 | 4-Br | H | $C_2H_5$ | 6-$CH_3$ | H | $C_2H_5$ | H |
| 93 | 4-$CH_3O$ | $C_6H_5CH_2$ | $CH_3$ | H | H | COOH | H |
| 94 | H | $C_2H_5$ | $CH_3$ | H | H | $C_2H_5$ | 6-$CH_3$ |
| 95 | 4-$C_2H_5O$ | n-$C_8H_{17}$ | $CH_3$ | H | 4-$BrC_6H_4CH_2$ | i-$C_3H_7$ | H |

It is contemplated that by following procedures similar to those described in foregoing Example 39 but employing the appropriate [(X)(Y)(1-$R^9$-2-carboxy-5/6-$R^{11}$-indol-3-yl)]methane and dimethyl sulfate, diethyl sulfate or the appropriate B'-halogen, there will be obtained the [(X)(Y)(1-$R^9$-2-B'O-carbonyl-5/6-$R^{11}$-indol-3-yl)]methanes of Formula VIII, Examples 96–106, presented in Table F hereinbelow.

TABLE F

| | METHANES OF FORMULA VIII | | | | |
|---|---|---|---|---|---|
| Example | X | Y | $R^9$ | $R^{11}$ | B' |
| 96 | 2,4-[$(CH_3)_2N]_2C_6H_3$ | 2-$CH_3O$—4-$(C_2H_5)_2NC_6H_3$ | H | 5-Cl | n-$C_4H_9$ |
| 97 | 2,4-[$(CH_3)_2N]_2C_6H_3$ | 2-$C_2H_5O$—4-$(C_2H_5)_2NC_6H_3$ | H | 5-$CH_3O$ | n-$C_6H_{11}$ |
| 98 | 4-$(CH_3)(C_6H_5CH_2)NC_6H_3$ | 1-i-$C_3H_7$—indol-3-yl | H | 5-Cl | $C_6H_5CH_2$ |
| 99 | 2-$C_2H_5OC_6H_4$ | 1-$C_2H_4$—2-$CH_3$—indol-3-yl | $CH_3$ | H | n-$C_6H_{13}$ |
| 100 | 4-$ClC_6H_4$ | 1-i-$C_5H_{11}$—5-$CH_3O$—indol-3-yl | $CH_3$ | H | 4-$ClC_6H_4CH_2$ |
| 101 | 4-$(C_2H_5)(C_6H_5CH_2)NC_6H_3$ | 9-julolidinyl | H | H | n-$C_{16}H_{33}$ |
| 102 | 2-n-$C_4H_9OC_6H_4$ | 9-julolidinyl | H | 5-Cl | 4-$CH_3C_6H_4CH_2$ |

TABLE F-continued

| | METHANES OF FORMULA VIII | | | | |
|---|---|---|---|---|---|
| Example | X | Y | $R^9$ | $R^{11}$ | B' |
| 103 | 3-$NO_2C_6H_4$ | 9-julolidinyl | H | H | i-$C_3H_7$ |
| 104 | 2-$CH_3$—4-$NO_2C_6H_3$ | 9-julolidinyl | H | 5-$CH_3O$ | i-$C_8H_{17}$ |
| 105 | 2-thienyl | 2,4-[($C_2H_5$)$_2$N]$_2C_6H_3$ | H | 5-$CH_3O$ | 4-$BrC_6H_4CH_2$ |
| 106 | 2-thienyl | 2,4-($CH_3$)$_2C_6H_3$ | H | H | $C_4H_7$ |

EXAMPLE 107

The use of the compounds of Formulas I, X, XI, XII and XIII described in Examples 1 through 106, as color-forming components in pressure-sensitive microencapsulated copying systems is illustrated with reference to the product of Example 1.

A. A mixture of 60.0 g of i-propylbiphenyl and 1.46 g of [bis(4-dimethylaminophenyl)(1-ethyl-2-methylindol-3-yl)]methane, prepared as described above in Example 1 was heated to 95° C. until a clear solution was formed and then cooled to approximately 50° C. A second solution of 5.0 g of carboxymethylcellulose dissolved in 200.0 ml of distilled water was prepared. A third solution containing 15.0 g of 275 Bloom gelatin dissolved in 120.0 ml of distilled water was heated at approximately 50° C. for about one hour.

B. Two solutions, the first containing the product and the i-propylbiphenyl, and the second containing the carboxymethylcellulose and the water were mixed and emulsified using a variable speed one-half horsepower Eppenbach Homo-Mixer (Gifford-Wood Co., Hudson, N.Y.) for approximately fifteen minutes at an applied voltage of 30 volts until the particle size of the suspended emulsion was approximately 5 microns at approximately 50° C. While maintaining the rapid agitation, the third solution containing the gelatin and water was added and the pH adjusted to 6.5 with the addition of 10 percent aqueous sodium hydroxide. Slowly 670.0 ml of distilled water at approximately 50° C. was added and the pH was adjusted to 4.5 by the addition of 10 percent aqueous acetic acid. After five minutes of rapid agitation the mixture was cooled to approximately 15° C. by means of an external ice-water bath and 10.0 ml of a twenty-five percent glutaraldehyde solution was added dropwise and agitation continued for 15 minutes. At this time, the Eppenbach Homo-Mixer was replaced with a conventional blade type laboratory agitator and the suspension was stirred overnight. The suspension was adjusted to 1120.0 g with the addition of distilled water.

C. The stock microcapsule suspension prepared in part B above was coated on paper sheets to a thickness of approximately 0.0015 inch and the coated paper air dried. The paper thus coated with the microencapsulated colorless precursor was assembled as the top sheet in a manifold system by positioning the coated side in contact with the coated side of a commercially-available receiving sheet coated with a color developer of the electron-accepting type. More specifically, papers coated with a phenolic resin and with an acidic clay were employed in this test. An image was then drawn with a stylus on the top sheet bearing the microencapsulated colorless precursor on its reverse side causing the effected microcapsules to rupture thus allowing the solution of the colorless precursor held by said microcapsules to flow into contact with the color-developing substance on the receiving sheet whereupon a violet-colored image slowly formed. The developed image exhibited good tinctorial strength and excellent xerographic copiability characteristics.

When evaluated in a duplicating system prepared and tested as described above, the product of Example 3, [(4-dimethylaminophenyl)(1-ethyl-2-methylindolyl)(2-methylindol-3-yl)]methane, produced a blue-red-colored image; and the product of Example 5, [(2-thieny)(1-ethyl-2-methylindol-3-yl)(2-methylindol-3-yl)]methane, produced a brown-colored image.

EXAMPLE 108

Proceeding in a manner similar to that described in Example 107 above, a mixture of 0.73 g of [(4-nitrophenyl)(2-ethoxy-4-diethylaminophenyl)(1-ethyl-2-methylindol-3-yl)]methane prepared as described in Example 29 above and 0.73 g of 2-anilino-3-methyl-6-diethylaminofluoran were encapsulated. The capsules were coated on paper and the paper was assembled into a manifold system. An image was then drawn on the top sheet bearing the microencapsulated colorless precursor on its reverse side causing the effected microcapsules to rupture thus allowing the solution of the mixture of colorless precursor held be said microcapsules to flow into contact with the color developing substance on the receiving sheet whereupon a red-black-colored image developed on the acidic clay-coated paper and a green-black-colored image developed on the resin coated paper. After 64 hours of exposure to air, the image on the acidic clay-coated paper had changed to a red-brown-colored image and the image on the resin-coated paper had changed to a gray-black-colored image.

EXAMPLE 109

The utility of the compounds of Formulas I, X, XI, XII and XIII whose preparations are described in the foregoing examples as color-forming components in thermal marking systems is illustrated by the incorporation and testing of the compound of Example 1, [bis(4-dimethylaminophenyl)(1-ethyl-2-methylindol-3-yl)]methane in a thermal-sensitive marking paper. The test paper was prepared by a procedure similar to that described in U.S. Pat. No. 3,539,375.

A. A mixture of 2.0 g of [bis(4-dimethylaminophenyl)(1-ethyl-2-methylindol-3-yl)]methane, 8.6 g of a ten percent aqueous solution of polyvinyl alcohol (approximately 99 percent hydrolyzed), 3.7 g of water and 31.6 g of 1/16 inch diameter zirconium grinding beads were charged into a container which was placed in a mechanical shaker. Shaking was effected for one hour. The zirconium beads were then removed by straining the mixture through a No. 40 sieve.

B. Similarly, a mixture of 9.8 g of 4,4'-isopropylidine diphenol (Bisphenol A), 42.0 g of a ten percent aqueous polyvinyl alcohol solution (approximately 99 percent hydrolyzed), 18.2 g of water and 221.2 g of 1/16 inch diameter zirconium grinding beads was charged into a container which was placed in a mechanical shaker. After shaking was effected for one hour, the zirconium beads were removed by straining through a No. 40 sieve.

C. A coating composition was prepared by mixing 2.1 g of the slurry from part A and 47.9 g of the slurry from part B. The mixture was then uniformly coated on sheets of paper at a thickness of approximately 0.0015 inch and the coated sheets air dried. The coated paper was tested by tracing a design on the coated side of the paper placed on a smooth flat surface with a stylus heated to approximately 125° C. A violet-colored image corresponding to the traced design promptly developed.

When evaluated in thermal marking paper prepared and tested as described above, the product of Example 5, [(2-thieny)(1-ethyl-2-methyl-3-indolyl)(2-methylindol-3-yl)]methane, produced a light brown-orange-colored image at approximately 125° C.; and the product of Example 4, [(1-ethyl-2-methylindol-3-yl)(4-dimethylaminophenyl)(indol-3-yl)]methane, produced a rose-pink-colored image at approximately 100° C.

EXAMPLE 110

The utility of the compounds of Formulas I, X, XI, XII and XIII whose preparations are described in the foregoing examples as color-forming components in thermal marking systems is illustrated by the incorporation and testing of the compound [(4-methoxyphenyl)-bis(1-ethyl-2-methylindol-3-yl)]methane in a thermal-sensitive marking paper. The test paper was prepared by a procedure similar to that described in U.S. Pat. No. 3,447,944.

A. A mixture of 7.60 g of oxidized starch dispersed in 30.0 ml of distilled water was heated at a temperature in the range of 90°–93° C. for approximately twenty minutes to effect solution. The solution was cooled to ambient temperature and set aside.

B. Similarly, a mixture of 15.0 g of disodium phosphate, 50.0 ml of distilled water and 2.8 g of sodium hydroxide was heated with stirring to effect complete solution. The resulting solution was maintained at a temperature in the range of 40°–50° C.

C. A mixture of 4.0 g of [(4-methoxyphenyl)-bis(1-ethyl-2-methylindol-3-yl)]methane, 3.3 g of the starch solution from part A above, 16.0 ml of distilled water, 4.1 g of the disodium phosphate solution from part B above and 20.0 g of glass shot was charged into a container which was placed onto a roller mill. Rolling was effected for approximately thirty minutes. The container was placed then in a mechanical shaker and shaking was effected for approximately thirty minutes. The glass beads were removed by straining the mixture through cotton gauze.

D. To a solution of 10.8 ml of distilled water, 14.2 g of disodium phosphate solution from part B above and 16.3 g of of starch solution from part A above, there was added slowly with stirring a mixture of 2.6 g of benzoyl peroxide and 5.6 g of oxidized starch. The resulting mixture was stirred vigorously using a Hamilton Beach No. 30 drinkmaster mixer for approximately thirty minutes.

E. With stirring 11.3 g of the dispersion containing the dyestyff from part C above was combined with 20.4 g of the dispersion containing the benzoyl peroxide from part D above. The mixture was then uniformly coated on sheets of paper at a thickness of approximately 0.0015 inch and the coated sheets were air dried. The coated paper was tested by tracing a design on the coated side of the paper placed on a smooth flat surface with two styli, one heated to approximately 100° C. and the second heated to 125° C. A rose-colored image corresponding to the traced design at 100° C. promptly developed and a brick red-colored image corresponding to the traced design at 125° C. promptly developed.

A series of six solutions were prepared by dissolving varying amounts of the compounds of Formulas I, X, XI, XII and XIII or mixtures thereof with other known colorless precursors in 50.0 ml of toluene. The colorless precursor solutions were then streaked on both an acidic clay-coated paper and an acidic resin-coated paper and the streaked paper exposed to the air for a period of twenty-four hours. The following table describes in column 1, the example number; in column 2, the weight and chemical name of the colorless precursor(s); in column 3, the source of the colorless precursor; and in column 4, the color of the developed image after twenty-four hours of air exposure on both acidic clay-and resin-coated paper.

TABLE G

| Example No. | Amount and Name of Colorless Precursor(s) | Source of Colorless Precursors | Color of Developed Image Clay Paper | Color of Developed Image Resin Paper |
|---|---|---|---|---|
| 111 | 1.0 g [(4-Methoxyphenyl)(2-ethoxy-4-diethylaminophenyl)(1-ethyl-2-methylindol-3-yl)]methane | Example 27 | red-brown | gray |
| 112 | 1.5 g 2-Anilino-3-methyl-6-diethyl-aminofluoran | * | red-brown | red-black |
| 113 | 1.0 g [(4-Methoxyphenyl)(2-ethoxy-4-diethylaminophenyl)(1-ethyl-2-methylindol-3-yl)]methane | Example 27 | dark red-brown | dark red-brown |
| | 1.5 g 2-Anilino-3-methyl-6-diethyl-aminofluoran | * | | |
| 114 | 1.0 g [(4-Methoxyphenyl)(2-ethoxy-4-diethylaminophenyl)(1-ethyl-2-methylindol-3-yl)]methane | Example 27 | dark red | black |
| | 1.5 g 2-N—Benzylamino-3-methyl-6-diethylamino-5'/6'-ethoxy-carbonylfluoran | ** | | |
| 115 | 1.0 g [(4-Methoxyphenyl)(2-ethoxy-4-diethylaminophenyl)(1-ethyl-2-methylindol-3-yl)]methane | Example 27 | dark red | dark red-black |
| | 0.5 g 3,3-Bis(1-n-butyl-2-methyl-indol-3-yl)phthalide | *** | | |
| | 1.5 g 2-N—Benzylamino-3-methyl-6-diethylamino-5'/6'-ethoxy-carbonylfluoran | ** | | |
| 116 | 1.0 g [(Phenyl)(4-dimethylamino- | Example 24 | red-black | black |

TABLE G-continued

| Example No. | Amount and Name of Colorless Precursor(s) | Source of Colorless Precursors | Color of Developed Image | |
|---|---|---|---|---|
| | | | Clay Paper | Resin Paper |
| | phenyl)(1,2-dimethylindol-3-yl)]methane | | | |
| | 1.5 g 2-Anilino-3-methyl-6-diethyl-aminofluoran | * | | |

*U.S. Pat. No. 3,681,370
**U.S. Pat. No. 4,274,660
***U.S. Pat. No. 3,509,173

We claim:

1. A [(2-R$^1$-3-R$^2$-4-R$^4$-phenyl)(9-julolidinyl)(1-R$^9$-2-R$^{10}$-5/6-R$^{11}$-indol-3-yl)]methane having the formula

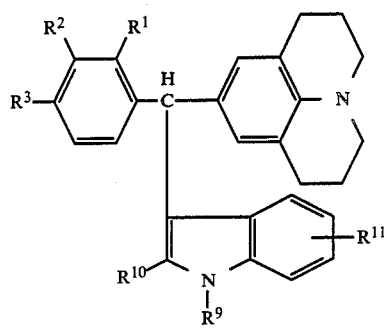

wherein:
R$^1$ represents hydrogen, C$_1$ to C$_3$ alkyl, non-tertiary C$_1$ to C$_4$ alkoxy, halo or dialkylamino in which alkyl is non-tertiary C$_1$ to C$_4$ alkyl;
R$^2$ represents hydrogen or nitro;
R$^3$ represents hydrogen, C$_1$ to C$_3$ alkyl, non-tertiary C$_1$ to C$_4$ alkoxy, halo, nitro, dialkylamino or N-alkylbenzylamino in which alkyl is non-tertiary C$_1$ to C$_4$ alkyl and benzyl may be substituted in the benzene ring by one or two of halo or alkyl;
R$^9$ represents hydrogen, C$_1$ to C$_{18}$ alkyl, C$_2$ to C$_4$ alkenyl, benzyl or benzyl substituted in the benzene ring by one or two of halo or C$_1$ to C$_3$ alkyl;
R$^{10}$ represents hydrogen, C$_1$ to C$_3$ alkyl, phenyl or $$-\overset{\overset{\displaystyle O}{\|}}{C}OB''$$

in which B" represents hydrogen, C$_1$ to C$_{18}$ alkyl, C$_2$ to C$_8$ alkenyl, benzyl or benzyl substituted in the benzene ring by C$_1$ to C$_{12}$ alkyl, halo or C$_1$ to C$_8$ alkoxy; and
R$^{11}$ represents one or two of hydrogen, C$_1$ to C$_3$ alkyl, C$_1$ to C$_3$ alkoxy, halo or nitro.

2. [(4-Dimethylaminophenyl)(9-julolidinyl)(1-ethyl-2-methylindol-3-yl)]methane according to claim 1.

3. A process for preparing a [(X)(Y)(1-R$^9$-2-R$^{10}$-5/6-R$^{11}$-indol-3-yl)]methane having the formula

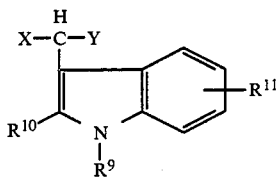

which comprises interacting a [(X)(Y)(R-phenylsulfonyl)]methane having the formula

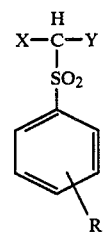

with an indole of the formula

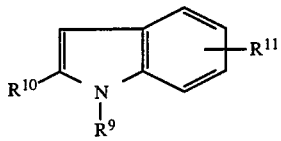

in the presence of an alkaline or an acid catalyst wherein:
X represents a moiety selected from the class having the formulas

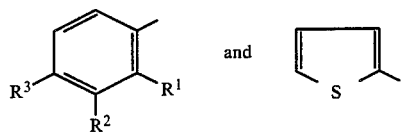

in which
R$^1$ represents hydrogen, C$_1$ to C$_3$ alkyl, non-tertiary C$_1$ to C$_4$ alkoxy, halo or dialkylamino in which alkyl is non-tertiary C$_1$ to C$_4$ alkyl,
R$^2$ represents hydrogen or nitro; and
R$^3$ represents hydrogen, C$_1$ to C$_3$ alkyl, non-tertiary C$_1$ to C$_4$ alkoxy, halo, nitro, dialkylamino or N-alkylbenzylamino in which alkyl is non-tertiary C$_1$ to C$_4$ alkyl and benzyl may be substituted in the benzene ring by one or two of halo or C$_1$ to C$_3$ alkyl;
Y represents a moiety selected from the group having the formulas

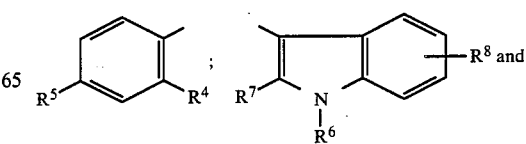

[structure: julolidine ring]

in which

R⁴ represents hydrogen, $C_1$ to $C_3$ alkyl, non-tertiary $C_1$ to $C_4$ alkoxy, halo or dialkylamino in which alkyl is non-tertiary $C_1$ to $C_4$ alkyl, R⁵ represents hydrogen, $C_1$ to $C_3$ alkyl, non-tertiary $C_1$ to $C_4$ alkoxy, halo, dialkylamino or N-alkylbenzylamino in which alkyl is a non-tertiary $C_1$ to $C_4$ alkyl and benzyl may be substituted in the benzene ring by one or two of halo or $C_1$ to $C_3$ alkyl, R⁶ represents hydrogen, non-tertiary $C_1$ to $C_{18}$ alkyl, $C_2$ to $C_4$ alkenyl, benzyl or benzyl substituted in the benzene ring by one or two of $C_1$ to $C_3$ alkyl or halo, R⁷ represents hydrogen, $C_1$ to $C_3$ alkyl or phenyl, and R⁸ represents one or two of hydrogen, $C_1$ to $C_3$ alkyl, $C_1$ to $C_3$ alkoxy, halo or nitro;

R⁹ represents hydrogen, non-tertiary $C_1$ to $C_{18}$ alkyl, $C_2$ to $C_4$ alkenyl, benzyl or benzyl substituted in the benzene ring by one or two of halo or $C_1$ to $C_3$ alkyl;

R¹⁰ represents hydrogen, $C_1$ to $C_3$ alkyl, phenyl or carboxy;

R¹¹ represents one or two of hydrogen, $C_1$ to $C_3$ alkyl, $C_1$ to $C_3$ alkoxy, halo or nitro; and R represents one or two of hydrogen, non-tertiary $C_1$ to $C_{12}$ alkyl, $C_1$ to $C_3$ alkoxy, halo, nitro or acetamido.

4. A process according to claim 3 wherein X is

[structure: benzene ring with R¹, R², R³]

and Y is

[structure: benzene ring with R⁴, R⁵]

in which R¹, R², R³, R⁴ and R⁵ each have the same respective meanings given in claim 3.

5. A process according to claim 3 wherein X is

[structure: benzene ring with R¹, R², R³]

and Y is

[structure: indole with R⁶, R⁷, R⁸]

in which R¹, R², R³, R⁶, R⁷ and R⁸ each have the same respective meanings given in claim 3.

6. A process according to claim 3 wherein X is

[structure: benzene ring with R¹, R², R³]

and Y is

[structure: julolidine]

in which R¹, R² and R³ each have the same respective meanings given in claim 3.

7. A process according to claim 3 wherein X is

[structure: thiophene]

and Y is

[structure: indole with R⁶, R⁷, R⁸]

in which R⁶, R⁷ and R⁸ each have the same respective meanings given in claim 3.

* * * * *